US012622760B2

(12) United States Patent
Rabindran et al.

(10) Patent No.: US 12,622,760 B2
(45) **Date of Patent: *May 12, 2026**

(54) COMPUTER-ASSISTED TELE-OPERATED SURGERY SYSTEMS AND METHODS

(71) Applicant: INTUITIVE SURGICAL OPERATIONS, INC., Sunnyvale, CA (US)

(72) Inventors: Dinesh Rabindran, San Jose, CA (US); Katherine Suzanne Anderson, Mountain View, CA (US); Nicholas Leo Bernstein, Cary, NC (US); Simon Peter Dimaio, San Carlos, CA (US); Catherine Mohr, Mountain View, CA (US); Theodore W. Rogers, San Jose, CA (US); Kollin Myles Tierling, Los Altos Hills, CA (US); Andrew Cullen Waterbury, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 60 days.

This patent is subject to a terminal disclaimer.

(21) Appl. No.: 18/582,518

(22) Filed: Feb. 20, 2024

(65) Prior Publication Data

US 2024/0189050 A1      Jun. 13, 2024

Related U.S. Application Data

(63) Continuation of application No. 18/160,851, filed on Jan. 27, 2023, now Pat. No. 11,950,870, which is a
(Continued)

(51) Int. Cl.
*B25J 9/16* (2006.01)
*A61B 34/30* (2016.01)
(Continued)

(52) U.S. Cl.
CPC .............. *A61B 34/35* (2016.02); *A61B 90/03* (2016.02); *A61B 90/06* (2016.02); *B25J 9/1697* (2013.01);
(Continued)

(58) Field of Classification Search
CPC ......... A61B 34/35; A61B 90/03; A61B 90/06; A61B 1/00193; A61B 17/29;
(Continued)

(56) References Cited

U.S. PATENT DOCUMENTS

| | | | |
|---|---|---|---|
| 5,122,122 A | 6/1992 | Allgood |
| 5,318,012 A | 6/1994 | Wilk |

(Continued)

FOREIGN PATENT DOCUMENTS

| | | |
|---|---|---|
| CN | 102697559 A | 10/2012 |
| CN | 104042344 A | 9/2014 |

(Continued)

OTHER PUBLICATIONS

International Search Report and Written Opinion for Application No. PCT/US2017/036306, mailed on Sep. 12, 2017, 13 pages (ISRG06620/PCT).

(Continued)

*Primary Examiner* — Dylan M Katz
(74) *Attorney, Agent, or Firm* — Artegis Law Group, LLP

(57) ABSTRACT

A computer-assisted system includes a manipulator assembly configured to couple to a cannula at a distal portion of the manipulator assembly. The cannula has a lumen configured to receive a shaft of an instrument. A cannula axis is aligned with the cannula when the cannula is coupled to the manipulator assembly. An instrument axis is aligned with the instrument when the instrument is coupled to the manipulator assembly. A controller coupled to the manipulator assembly is configured to receive an indication to reposition
(Continued)

a remote center of motion (RCM) for the manipulator assembly while the RCM is positioned at a first location relative to the distal portion along an axis, wherein the axis is aligned with the cannula axis or the instrument axis; and in response to receiving the indication, cause the RCM to be positioned at a second location relative to the distal portion along the axis.

20 Claims, 21 Drawing Sheets

Related U.S. Application Data continuation of application No. 16/305,203, filed as application No. PCT/US2017/036306 on Jun. 7, 2017, now Pat. No. 11,596,486.

(60) Provisional application No. 62/347,961, filed on Jun. 9, 2016.

(51) Int. Cl.

| | |
|---|---|
| *A61B 34/35* | (2016.01) |
| *A61B 90/00* | (2016.01) |
| *A61B 1/00* | (2006.01) |
| *A61B 17/00* | (2006.01) |
| *A61B 17/29* | (2006.01) |
| *A61B 17/34* | (2006.01) |

(52) U.S. Cl.

CPC . *A61B 1/00193* (2013.01); *A61B 2017/00212* (2013.01); *A61B 2017/00557* (2013.01); *A61B 2017/00561* (2013.01); *A61B 17/29* (2013.01); *A61B 17/3423* (2013.01); *A61B 17/3468* (2013.01); *A61B 2034/301* (2016.02); *A61B 2034/302* (2016.02); *A61B 2090/064* (2016.02); *A61B 2217/005* (2013.01)

(58) Field of Classification Search

CPC ............ A61B 17/3423; A61B 17/3468; A61B 2017/00212; A61B 2017/00557; A61B 2017/00561; A61B 2034/301; A61B 2034/302; A61B 2090/064; A61B 2217/005; A61B 2090/0811; A61B 34/77; A61B 34/37; A61B 2090/0807; A61B 17/0218; A61B 34/00; A61B 2017/3409; A61B 2017/3447; A61B 2017/3486; A61B 2034/742; A61B 34/10; A61B 17/3415; A61B 34/70; A61B 2017/0237; A61B 2034/101; A61B 17/00234; A61B 17/0281; B25J 9/1697

See application file for complete search history.

(56) References Cited

U.S. PATENT DOCUMENTS

| | | | |
|---|---|---|---|
| 5,397,323 | A | 3/1995 | Taylor et al. |
| 5,637,097 | A | 6/1997 | Yoon |
| 5,649,956 | A | 7/1997 | Jensen et al. |
| 5,779,623 | A | 7/1998 | Bonnell |
| 5,836,871 | A | 11/1998 | Wallace et al. |
| 6,451,027 | B1 | 9/2002 | Cooper et al. |
| 8,151,661 | B2 | 4/2012 | Schena et al. |
| 11,596,486 | B2 | 3/2023 | Rabindran et al. |
| 11,950,870 | B2 * | 4/2024 | Rabindran ............. B25J 9/1697 |
| 2003/0109780 | A1 | 6/2003 | Coste-Maniere et al. |
| 2010/0204713 | A1 | 8/2010 | Ruiz Morales |
| 2011/0213383 | A1 | 9/2011 | Lee et al. |
| 2013/0116706 | A1 | 5/2013 | Lee et al. |
| 2013/0274761 | A1 | 10/2013 | Devengenzo et al. |
| 2014/0194699 | A1 | 7/2014 | Roh et al. |
| 2014/0222207 | A1 | 8/2014 | Bowling et al. |
| 2014/0276953 | A1 | 9/2014 | Swarup et al. |
| 2014/0277736 | A1 | 9/2014 | Itkowitz et al. |
| 2015/0045814 | A1 | 2/2015 | Prisco et al. |
| 2015/0065793 | A1 | 3/2015 | Diolaiti et al. |
| 2015/0133739 | A1 | 5/2015 | Piskun et al. |
| 2016/0000512 | A1 | 1/2016 | Gombert et al. |
| 2016/0235490 | A1 | 8/2016 | Srivastava et al. |
| 2017/0020615 | A1 | 1/2017 | Koenig et al. |
| 2018/0049737 | A1 | 2/2018 | Swayze et al. |
| 2019/0133704 | A1 * | 5/2019 | Hiratsuka ............. A61B 34/37 |
| 2023/0172677 | A1 | 6/2023 | Rabindran et al. |

FOREIGN PATENT DOCUMENTS

| | | | |
|---|---|---|---|
| KR | 101413406 | B1 | 6/2014 |
| KR | 20140090374 | A | 7/2014 |
| KR | 20140113209 | A | 9/2014 |
| KR | 20150003612 | U | 10/2015 |
| WO | WO-9720504 | A1 | 6/1997 |
| WO | WO-2006124390 | A2 | 11/2006 |
| WO | WO-2011037718 | A1 | 3/2011 |
| WO | WO-2011060046 | A2 | 5/2011 |
| WO | WO-2013181507 | A1 | 12/2013 |
| WO | WO-2014114551 | A1 | 7/2014 |
| WO | WO-2014146107 | A1 | 9/2014 |
| WO | WO-2015052629 | A1 | 4/2015 |
| WO | WO-2015127078 | A1 | 8/2015 |
| WO | WO-2015175200 | A1 | 11/2015 |
| WO | WO-2016043845 | A1 | 3/2016 |
| WO | WO-2016064616 | A1 | 4/2016 |
| WO | WO-2016090459 | A1 | 6/2016 |
| WO | WO-2016144998 | A1 | 9/2016 |
| WO | WO-2016183054 | A1 | 11/2016 |

OTHER PUBLICATIONS

International Search Report and Written Opinion for Application No. PCT/US2017/051846, mailed on Jan. 10, 2018, 11 pages (ISRG08990/PCT).

Long J.A., et al., "Development of Miniaturized Light Endoscope-holder Robot for Laparoscopic Surgery," Journal of Endourology, Aug. 2007, vol. 21 (8), pp. 911-914.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

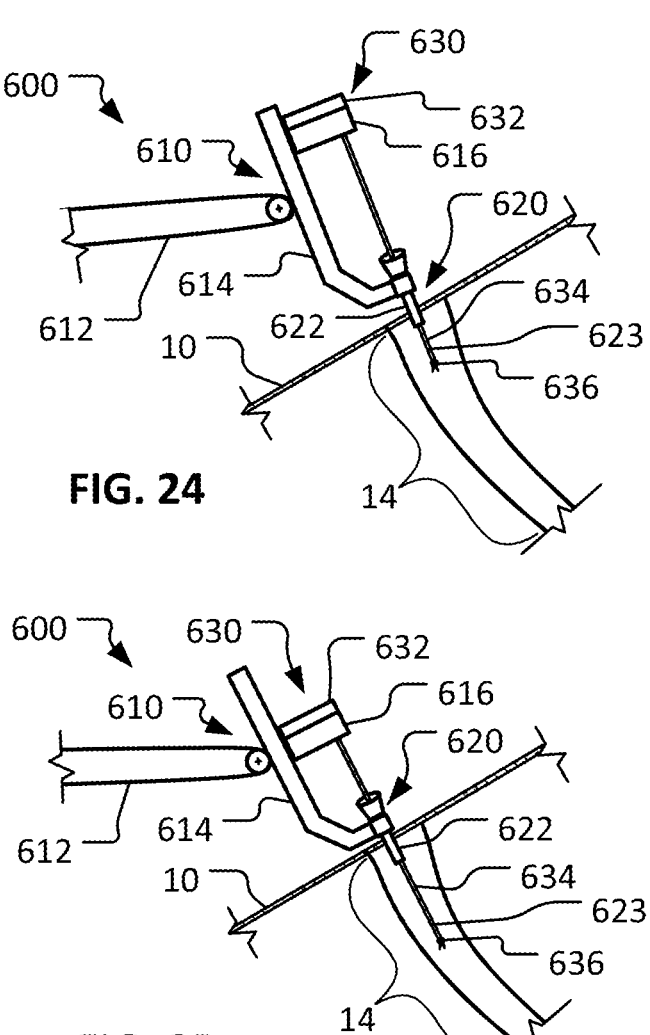
FIG. 24
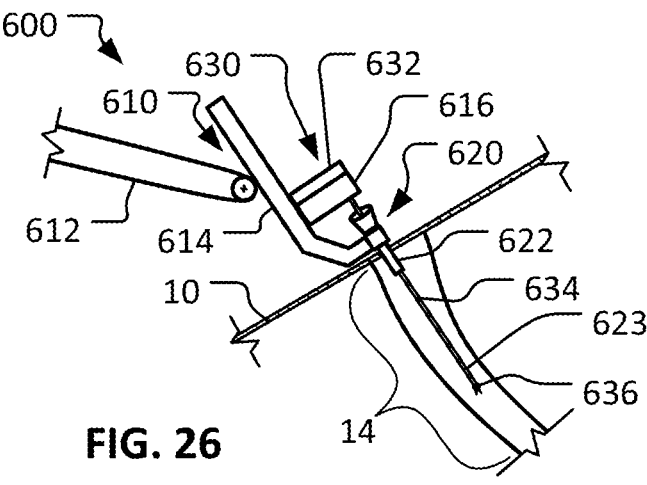
FIG. 25
FIG. 26

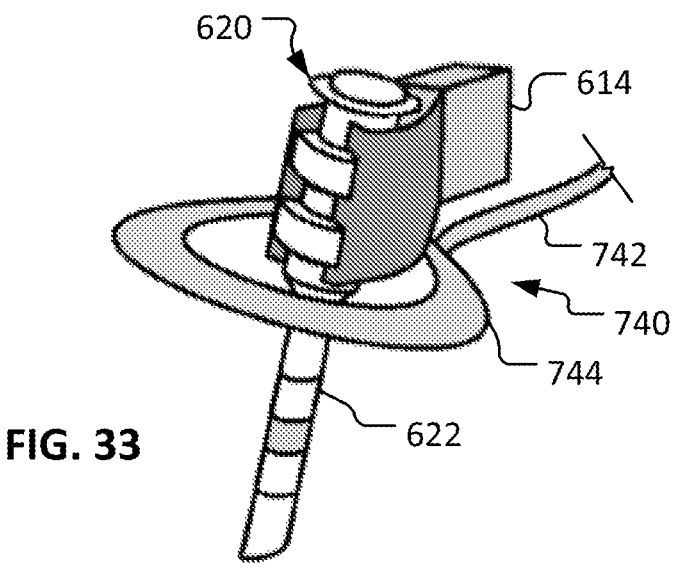
FIG. 33
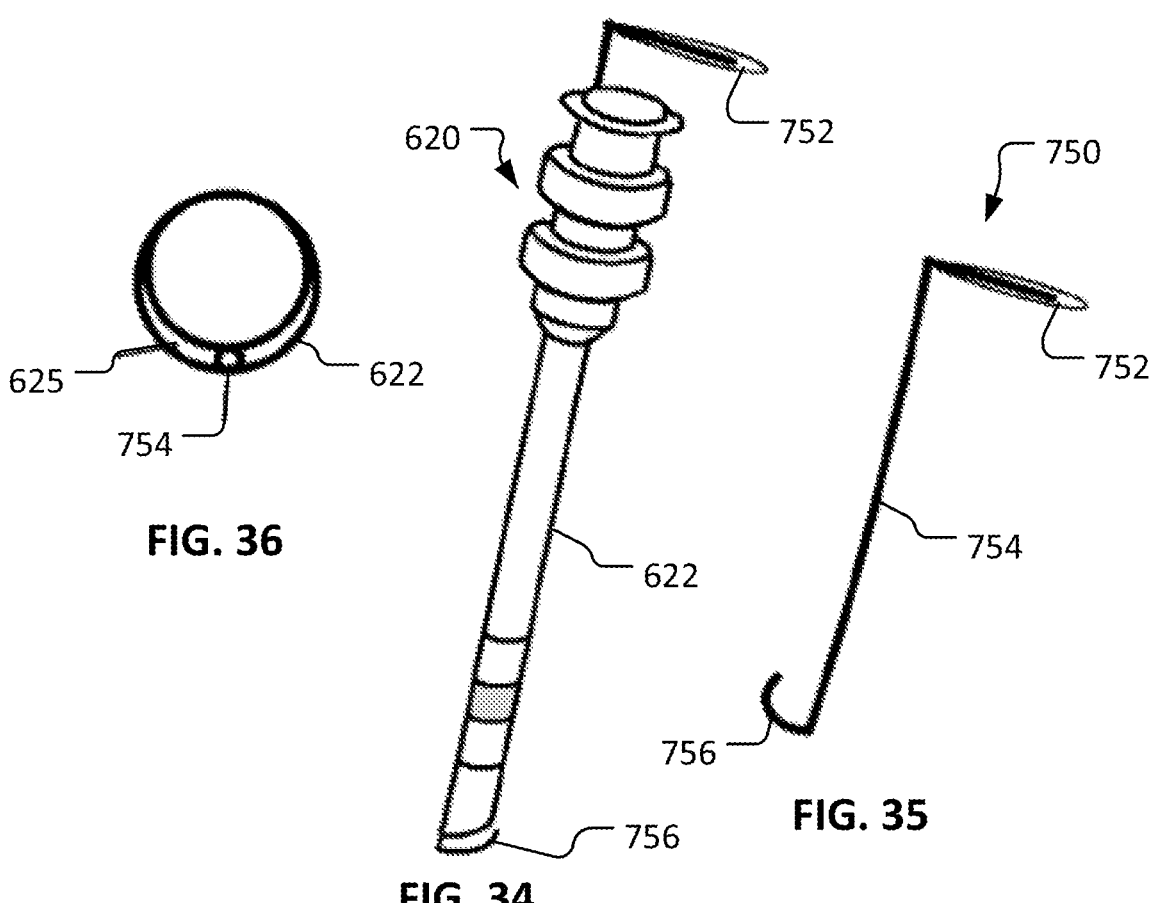
FIG. 36
FIG. 34
FIG. 35

Body Wall Tented

Cannula Motion Constrained Along Instrument Shaft

620

622

636

624

634

10

41

Left Master (Controlling Instruments Tip Frame)

Right Master Constrained so that Cannula Motion is Along Instrument Shaft

Right Master (Controlling RCM Frame)

42

631

COMPUTER-ASSISTED TELE-OPERATED SURGERY SYSTEMS AND METHODS

CROSS REFERENCE TO RELATED APPLICATIONS

This application is a continuation of U.S. patent application Ser. No. 18/160,851, filed Jan. 27, 2023, which is a continuation of U.S. patent application Ser. No. 16/305,203, filed Nov. 28, 2018, which is a U.S. National Stage Application of International Patent Application No. PCT/US2017/036306, filed Jun. 7, 2017, which claims the benefit of U.S. Provisional Application No. 62/347,961, filed Jun. 9, 2016. The disclosures of each of these prior applications is incorporated by reference in the disclosure of this application.

TECHNICAL FIELD

This disclosure relates to systems and methods for minimally invasive computer-assisted tele-operated surgery. For example, the disclosure relates to methods for controlling motions of a robotic manipulator, cannula, and surgical instrument in various surgical contexts.

BACKGROUND

Robotic systems and computer-assisted devices often include robot or movable arms to manipulate instruments for performing a task at a work site and at least one robot or movable arm for supporting an image capturing device which captures images of the work site. A robot arm comprises a plurality of links coupled together by one or more actively controlled joints. In many embodiments, a plurality of actively controlled joints may be provided. The robot arm may also include one or more passive joints, which are not actively controlled, but comply with movement of an actively controlled joint. Such active and passive joints may be revolute or prismatic joints. The configuration of the robot arm may then be determined by the positions of the joints and knowledge of the structure and coupling of the links.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments. The robotic surgical instruments can be inserted through small, minimally invasive surgical apertures to treat tissues at surgical sites within the patient, often the trauma associated with accessing for open surgery. These robotic systems can move the working ends or end-effectors of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

SUMMARY

This disclosure provides systems and methods for computer-assisted medical operations and non-medical operations. For example, the disclosure provides systems and methods for assisting minimally invasive computer-assisted tele-operated surgery (also referred to herein as "robotic surgery" and "computer-assisted surgery"). For example, the disclosure provides methods for controlling motions of the robotic manipulator, cannula, and surgical instrument in various surgical situations.

In the context of minimally invasive computer-assisted tele-operated surgery, movements of the robotic manipulator assembly may be controlled by a processor of the system so that a shaft or intermediate portion of the surgical instrument is constrained to a safe motion through a minimally invasive surgical access site or other aperture. Such motion may include, for example, axial insertion of the shaft through the aperture site, rotation of the shaft about its axis, and pivotal motion of the shaft about a pivot point adjacent the access site, but will often preclude excessive lateral motion of the shaft which might otherwise tear the tissues adjacent the aperture or enlarge the access site inadvertently. Some or all of such constraint on the robotic manipulator assembly motion at the access site may be imposed using in part or in full using robotic data processing and control techniques. Such concepts for constraining, by a processor of the computer-assisted surgery system, the robotic manipulator assembly motion may be referred to herein as software-constrained remote center of motion.

In some cases, methods using the software-constrained remote center of motion concepts for controlling of the robotic manipulator assembly can include locating, using a processor of the computer-assisted surgery system, the remote center of motion at locations other than on the cannula at the surgical access site. In one such example, this disclosure provides methods that use the software-constrained remote center of motion concepts to locate the remote center of motion at a fixed position on the shaft of the surgical instrument. Additionally or alternatively, the position of the remote center of motion may or may not be coincident with the surgical access site or aperture. In another such example, this disclosure provides methods that use the software-constrained remote center of motion concepts to locate the remote center of motion at a tissue layer within the patient's body. In cases such as these, the methods may allow at least some lateral motion of the cannula at the surgical access site or aperture.

In one aspect, this disclosure describes a computer-assisted surgery system. The computer-assisted surgery system includes a manipulator assembly configured to couple to a cannula, and a processor in electrical communication with the manipulator assembly. The cannula defines a lumen configured to slidably receive a shaft of a surgical instrument. The processor is configured to locate a remote center of motion for the manipulator assembly at a first location relative to the cannula, and to reposition the remote center of motion to a second location relative to the cannula in response to an indication to reposition the remote center of motion relative to the cannula. The second location is different from the first location.

Such a computer-assisted surgery system may optionally include one or more of the following features. In some embodiments, the first location is along the cannula and the second location is not along the cannula. In some embodiments, the first location and the second location are at different distances from a longitudinal axis defined by the cannula. The processor may be configured to reposition the remote center of motion to the second location while keeping or constraining the second location to within a maximum distance from the longitudinal axis. The processor may also be configured to limit a motion of the cannula based on the second location. The processor may also be configured to receive a command to move the instrument in accordance with a commanded instrument motion, and to command the instrument to move with a modified instrument motion. The modified instrument motion may be based on the commanded instrument motion and the second location. In some embodiments, the processor is configured to reposition the remote center of motion to the second location while keeping or constraining the second location along the cannula. The first location may coincident with an axis defined by the lumen of the cannula, and the processor may be configured to reposition the remote center of motion to the second location while keeping or constraining the second location coincident with the axis. The processor may be configured to reposition the remote center of motion to the second location while keeping or constraining the second location along a shaft of the instrument.

Further, such a computer-assisted surgery system may optionally include one or more of the following additional features. The processor may also be configured to output one or more signals to cause the manipulator assembly to move the cannula and the instrument relative to each other such that the first location and the second location are at a same location relative to the instrument. The processor may be configured to output the one or more signals to cause the manipulator assembly to move the cannula and the instrument relative to each other by outputting, by the processor, one or more signals to cause the manipulator assembly to move the instrument while holding the cannula stationary. The processor may be configured to reposition the remote center of motion to the second location while limiting a speed of motion of the remote center of motion. The processor may be configured to determine a force associated with the cannula, and disallow repositioning of the remote center of motion in response to the force associated with the cannula exceeding a force limit. The surgery system may also include a visual indicator, and the processor may be configured to provide a visual indication of the remote center of motion using the visual indicator. The cannula may be selectively couplable with a tissue layer of a patient such that the lumen is in communication with a surgical working space. The processor may be configured to move the cannula relative to patient anatomy such that the surgical working space is modified. In some cases, the tissue layer may be an inner tissue layer. In some cases, a body wall of the patient may comprise the tissue layer.

Still further, such a computer-assisted surgery system may optionally include one or more of the following additional features separately or in combination with any of the features described earlier. The processor may be configured to move the cannula relative to the patient anatomy such that the surgical working space is modified by: moving the cannula such that the surgical working space is changed in size (reduced in size or enlarged), or moving the cannula such that the surgical working space is changed in shape, or moving the cannula such that the surgical working space is changed in size (reduced or increased in size) and shape. The processor may be configured to move the cannula relative to the patient anatomy such that the surgical working space is modified by: (i) detecting a coupling of the cannula to the manipulator assembly (wherein the cannula is configured to couple with a tissue layer of a patient), and (ii) moving the manipulator assembly such that the cannula causes the tissue layer to tent and enlarge the surgical working space. The cannula may comprise an inflatable member configured to selectively couple the cannula with a tissue layer of a patient. The manipulator assembly may comprise a hook or a suction device for tenting tissue. The processor of the surgery system may be configured to generate the indication to reposition the remote center of motion relative to the cannula, or to receive (from external to the processor) the indication to reposition the remote center of motion relative to the cannula, or to generate the indication in some instances and to receive the indication in other instances. The surgery system may include an input means for a user to initiate the indication to reposition the remote center of motion relative to the cannula. The surgery system may comprise a second processor configured to provide the indication to the processor. The surgery system may include an operator console comprising a handheld input device, where the operator console provides the indication to reposition the remote center of motion in response to a signal from the handheld input device. The surgery system may include first and second handheld input devices in electrical communication with the processor, where the indication to reposition the remote center of motion comprises a signal indicating relative motion of the first handheld input device away from the second handheld input device. The surgery system may include a switch coupled to the manipulator assembly. Activation of the switch may send to the processor the indication to reposition the remote center of motion relative to the cannula. The surgery system may include a switch coupled to the manipulator assembly. Activation of the switch coupled to the manipulator assembly followed by a manual movement of the manipulator assembly may send to the processor the indication to reposition the remote center of motion relative to the cannula. The processor may be configured to perform one or more of: (a) detect a coupling of the cannula to the manipulator assembly (wherein the cannula may be configured to couple with a tissue layer of a patient); (b) detect a second coupling of a second cannula to a second manipulator assembly of the surgery system (wherein the second cannula may be configured to couple with the tissue layer of a patient); and (c) move the manipulator assembly and the second manipulator assembly contemporaneously such that the cannula and the second cannula deform the tissue layer and modify a surgical working space. The surgery system may cause the tissue layer to deform and modify the surgical working space by moving the manipulator assembly and the second manipulator assembly such that the cannula and the second cannula cause the tissue layer to tent and enlarge the surgical working space.

In another aspect, this disclosure describes a computer-assisted robotic method. The computer-assisted robotic method includes determining, by a processor of a computer-assisted robotic system, a first location of a remote center of motion of the robotic system. The robotic system includes a manipulator assembly and a cannula couplable with the manipulator assembly. The cannula defines a lumen configured to slidably receive a shaft of an instrument. The computer-assisted robotic method also includes receiving, by the processor, an indication to reposition the remote center of motion relative to the cannula, and repositioning, by the processor and in response to receiving the indication, the remote center of motion to a second location relative to the cannula.

Such a computer-assisted robotic method may optionally include one or more of the following features. In some cases, the first location is along the cannula and the second location is not along the cannula. The first location and the second location may be at different distances from a longitudinal axis defined by the cannula. Repositioning the remote center of motion to the second location may include keeping or constraining the second location to within a maximum distance from the longitudinal axis. The method may also include limiting a motion of the cannula based on the second location. The method may also include receiving a command to move the instrument with a commanded instrument motion, and commanding the instrument to move with a modified instrument motion. The modified instrument motion may be based on the commanded instrument motion and the second location. The repositioning the remote center of motion to the second location may include keeping or constraining the second location along the cannula. The first location may be coincident with an axis defined by the lumen. The repositioning the remote center of motion to the second location may include keeping or constraining the second location to coincide with the axis defined by the lumen. The repositioning the remote center of motion to the second location may include keeping or constraining the second location along a shaft of the instrument.

Further, such a computer-assisted robotic method may optionally include one or more of the following additional features separately or in combination with any of the features described earlier. The robotic system may also include the instrument. The method may also include outputting, by the processor, one or more signals to cause the manipulator assembly to move the cannula and the instrument relative to each other such that the first location and the second location are at a same location relative to the instrument. The outputting, by the processor, one or more signals to cause the manipulator assembly to move the cannula and the instrument relative to each other may include outputting, by the processor, one or more signals to cause the manipulator assembly to move the instrument while holding the cannula stationary. The repositioning the remote center of motion to the second location may include limiting a speed of motion of the remote center of motion. The method may also include determining a force associated with the cannula, and disallowing motion of the remote center of motion in response to the force associated with the cannula exceeding a force limit. The method may also include providing a visual indication of the remote center of motion.

In another aspect, this disclosure describes a non-transitory machine-readable medium comprising a plurality of machine-readable instructions which when executed by one or more processors associated with a computer-assisted surgery system are adapted to cause the one or more processors to perform a method. The method includes: (i) detecting a releasable coupling of a cannula to a manipulator assembly of the computer-assisted surgery system (the cannula defining a lumen and configured to couple with a tissue layer of a patient); (ii) detecting an installation of a surgical instrument to the manipulator assembly (a shaft of the surgical instrument defining a longitudinal axis and configured to extend through the lumen of the cannula such that a distal end portion of the shaft is located in a surgical working space within the patient); and (iii) causing the manipulator assembly to move such that the cannula moves along the longitudinal axis and modifies the surgical working space.

Such a method that the one or more processors associated with the computer-assisted surgery system are caused to perform by executing the plurality of machine-readable instructions may optionally include one or more of the following additional features. The step of causing the manipulator assembly to move such that the cannula moves along the longitudinal axis and modifies the surgical working space may include causing the manipulator assembly to move such that the cannula causes the tissue layer to tent and enlarge the working space. The step of causing the manipulator assembly to move such that the cannula moves along the longitudinal axis and modifies the surgical working space may include receiving an actuation signal from a switch coupled to the manipulator assembly, and moving the manipulator assembly. The step of causing the manipulator assembly to move such that the cannula moves along the longitudinal axis and modifies the surgical working space may include receiving input from a first handheld input device away from a second handheld input device, and moving the manipulator assembly. The method may also include keeping or constraining the surgical instrument substantially stationary while causing the manipulator assembly to move such that the cannula moves along the longitudinal axis and modifies the surgical working space. The method may also include detecting a releasable coupling of a second cannula to a second manipulator assembly of the computer-assisted surgery system. The second cannula may be configured to couple with the tissue layer of a patient. The step of causing the manipulator assembly to move such that the cannula moves along the longitudinal axis and modifies the surgical working space include moving the manipulator assembly and the second manipulator assembly contemporaneously such that the cannula and the second cannula cause the tissue layer to tent. The step of moving the manipulator assembly and the second manipulator assembly contemporaneously may include limiting contemporaneous movement of the manipulator assembly and the second manipulator assembly based on a shared remote center of motion.

In another aspect, this disclosure describes a computer-assisted tele-operated surgery method includes: (a) releasably coupling a cannula with a body wall of a patient, wherein the cannula defines a lumen and is couplable to a robotic manipulator arm assembly; (b) installing a shaft of a surgical instrument within the lumen of the cannula such that a distal end portion of the shaft is located in a surgical working space within the patient, wherein the shaft defines a longitudinal axis; and (c) moving the robotic manipulator arm assembly to cause the cannula to move along a fixed line in space that is coincident with the longitudinal axis, and wherein moving the cannula causes the body wall to tent such that the surgical working space is changed in size (reduced in size or enlarged).

Such a computer-assisted tele-operated surgery method may optionally include one or more of the following features. While the robotic manipulator arm assembly moves to cause the cannula to move, the position of the surgical instrument may be controlled independent of cannula motion. Moving the robotic manipulator arm may include actuating a switch coupled to the robotic manipulator arm. The moving the robotic manipulator arm may include moving a first master input device of an operator console such as a surgeon console away from a second master input device of the operator console. The cannula may be releasably coupled with the body wall using an inflatable member that is attached to the cannula. While the inflatable member is in an inflated configuration the cannula may be couplable with the body wall, and wherein while the inflatable member is in a deflated configuration the cannula may be uncoupled from the body wall.

In another aspect, this disclosure describes a computer-assisted tele-operated surgery method includes: (i) inserting, using a robotic manipulator arm assembly, an elongate surgical instrument into a surgical working space within a patient, wherein the surgical instrument includes a shaft and an end effector at a distal end of the shaft, wherein a remote center of motion of the robotic manipulator arm assembly is located at a first location coincident with the shaft or off-axis; and (ii) after the inserting, moving the surgical instrument farther distally into the surgical working space, wherein the remote center of motion remains located at the first location during the moving.

Such a computer-assisted tele-operated surgery method may optionally include one or more of the following features. Moving the surgical instrument may include moving the remote center of motion linearly. Moving the surgical instrument may include moving the remote center of motion along a curved path. The surgical working space may be an elongate channel or may be bordered by sensitive structures.

In another aspect, this disclosure describes a computer-assisted tele-operated surgery method includes: (1) inserting a cannula through a body wall of a patient and through an inner tissue layer of the patient, wherein the inner tissue layer is farther within the patient than the body wall, wherein the cannula defines a lumen and is couplable to a robotic manipulator arm assembly; (2) releasably coupling the cannula with the inner tissue layer; (3) installing a shaft of a surgical instrument within the lumen of the cannula such that a distal end portion of the shaft extends beyond a distal tip of the cannula and into a surgical working space within the patient, wherein the shaft defines a longitudinal axis; and (4) moving the robotic manipulator arm to cause the cannula to move along a fixed line in space that is coincident with the longitudinal axis, and wherein moving the cannula causes the inner tissue layer to tent such that the surgical working space is changed in size (reduced in size or enlarged) or manipulated (changed in shape, location, etc.) to assist with a task.

Such a computer-assisted tele-operated surgery method may optionally include one or more of the following features. While the robotic manipulator arm assembly moves to cause the cannula to move, the position of the surgical instrument may be maintained substantially stationary. Moving the robotic manipulator arm may include actuating a switch coupled to the robotic manipulator arm. Moving the robotic manipulator arm may include moving a first master input device of an operator console, such as a surgeon console, away from a second master input device of the operator console. The cannula may be releasably coupled with the inner tissue layer using an inflatable member that is attached to the cannula. While the inflatable member is in an inflated configuration the cannula may be couplable with the inner tissue layer, and wherein while the inflatable member is in a deflated configuration the cannula may be uncoupled from the inner tissue layer.

In another aspect, this disclosure describes a computer-assisted tele-operated surgery method includes: (i) coupling a port device with a body wall of a patient, wherein the port device defines a first lumen and a second lumen; (ii) slidably engaging a first cannula with the first lumen such that a distal end portion of the first cannula is positioned within a surgical working space of the patient; (iii) coupling the first cannula to a first robotic manipulator arm assembly; (iv) slidably engaging a second cannula with the second lumen such that a distal end portion of the second cannula is positioned within the surgical working space; (v) coupling the second cannula to a second robotic manipulator arm assembly; (vi) installing a shaft of a first surgical instrument within a lumen of the first cannula such that a distal end portion of the first surgical instrument is positioned within the surgical working space; (vii) installing a shaft of a second surgical instrument within a lumen of the second cannula such that a distal end portion of the second surgical instrument is positioned within the surgical working space; and (viii) moving the first robotic manipulator arm assembly and the second robotic manipulator arm assembly contemporaneously to thereby move the port device to modify the surgical working space.

Such a computer-assisted tele-operated surgery method may optionally include one or more of the following features. The contemporaneous movement of the first robotic manipulator arm assembly and the second robotic manipulator arm assembly may cause the body wall to become tented. The contemporaneous movement of the first robotic manipulator arm assembly and the second robotic manipulator arm assembly may be initiated at a remote surgeon console that can be used to control movements of the first robotic manipulator arm assembly and the second robotic manipulator arm assembly. The contemporaneous movement of the first robotic manipulator arm assembly and the second robotic manipulator arm assembly may be limited to a maximum allowable movement distance of a shared remote center of motion.

Some or all of the embodiments described herein may provide one or more of the following advantages. First, some computer-assisted tele-operated surgery methods provided herein facilitate tenting of the body wall through which the surgical access incision is made. Such methods provide various advantages, such as better visibility in the surgical working space. More room in the working space for better access is also facilitated using the tenting methods provided herein. The methods for tenting of the body wall may have advantages when employed to complement insufflation (or as an alternative to insufflation in some cases). For example, while insufflation facilitates generally symmetrical enlargement of the surgical working space, tissue deformation such as tenting can facilitate changes to parts of the working space, including asymmetrical enlargement or reduction of parts or all of the surgical working space. For example, for surgical working spaces that are shallow, or that have the entry point and operative points close together, asymmetrical enlargement can result in greater enlargement of the surgical working space than symmetrical enlargement. Also, for medical and non-medical procedures, control over the size, shape, and location of the working space can help facilitate steps in the procedure.

Second, some computer-assisted tele-operated surgery methods provided herein facilitate safe minimally invasive surgical access along channels within a patient's body. As described further below, some channels may be curved or irregularly shaped and are therefore challenging to navigate deep into the channel using conventional techniques. Using the software-constrained remote center of motion concepts described herein, in some embodiments the remote center of motion can be positioned on the shaft of the surgical instrument such that the location of the remote center of motion advances in the channel along with advancement of the surgical instrument. Such a technique can provide fine control of the distal end portion of the surgical instrument, thereby facilitating safe minimally invasive surgical access along the channel.

Third, some computer-assisted tele-operated surgery methods provided herein facilitate location of the remote center of motion at a layer of tissue within the patient's body. Such a technique may be particularly beneficial when the inner layer of tissue is more sensitive to lateral motion than the external body wall. For example, in the case of minimally invasive heart surgery (when the surgical working space is internal to the heart), the incision through the heart wall may be more sensitive to lateral motion than the incision through the chest wall. Using the software-constrained remote center of motion concepts described herein, the remote center of motion can be positioned at the site of the incision through the inner layer of tissue to thereby minimize lateral motion of the inner layer of tissue.

The details of one or more embodiments are set forth in the accompanying drawings and the description below. Other features, objects, and advantages will be apparent from the description and drawings, and from the claims.

BRIEF DESCRIPTION OF THE DRAWINGS

FIGS. 24-26 illustrate a minimally invasive computer-assisted tele-operated surgery method for operating within a channel-like surgical working space.

FIG. 33 is a robotic surgery cannula with an example tissue coupling element that can be used to create a tissue tent in accordance with the methods provided herein.

FIGS. 34-36 is a robotic surgery cannula with another example tissue coupling element that can be used to create a tissue tent in accordance with the methods provided herein.

Like reference symbols in the various drawings indicate like elements.

DETAILED DESCRIPTION

Figures 1, 2:
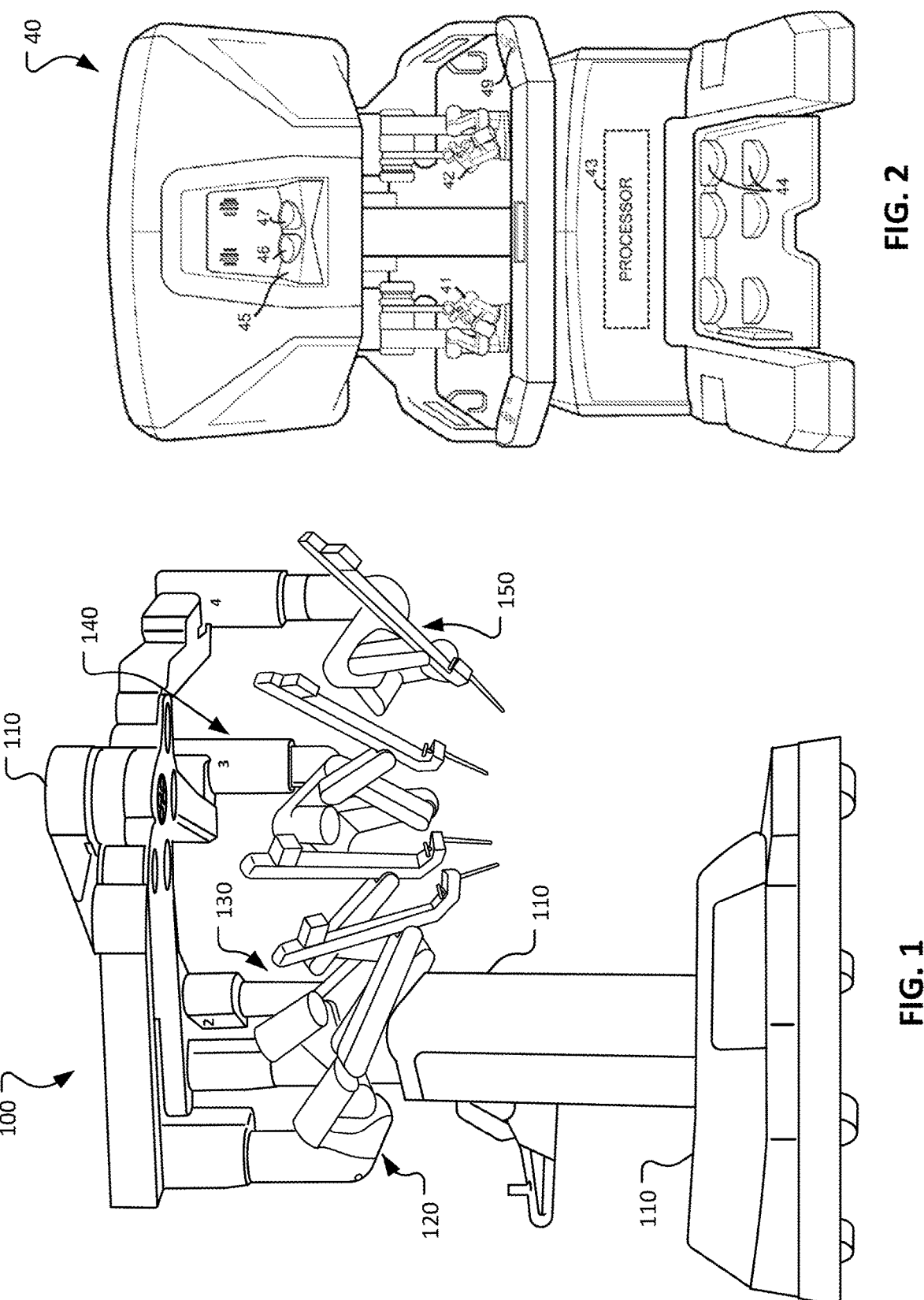
FIG. 1 is a perspective view of an example patient-side cart of a computer-assisted tele-operated surgery or robotic surgery system.
FIG. 2 is a front view of an example surgeon console of a computer-assisted tele-operated surgery system.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various special device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. The words "including" or "having" mean including but not limited to.

It should be understood that although this description is made to be sufficiently clear, concise, and exact, scrupulous and exhaustive linguistic precision is not always possible or desirable, since the description should be kept to a reasonable length and skilled readers will understand background and associated technology. For example, considering a video signal, a skilled reader will understand that an oscilloscope described as displaying the signal does not display the signal itself but a representation of the signal, and that a video monitor described as displaying the signal does not display the signal itself but video information the signal carries.

In addition, the singular forms "a", "an", and "the" are intended to include the plural forms as well, unless the context indicates otherwise. And, the terms "comprises", "includes", "has", and the like specify the presence of stated features, steps, operations, elements, and/or components but do not preclude the presence or addition of one or more other features, steps, operations, elements, components, and/or groups. And, the or each of the one or more individual listed items should be considered optional unless otherwise stated, so that various combinations of items are described without an exhaustive list of each possible combination. The auxiliary verb may likewise implies that a feature, step, operation, element, or component is optional.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Elements described as coupled may be electrically or mechanically directly coupled, or they may be indirectly coupled via one or more intermediate components.

The term "flexible" in association with a part, such as a mechanical structure, component, or component assembly, should be broadly construed. In essence, the term means the part can be repeatedly bent and restored to an original shape without harm to the part. Many "rigid" objects have a slight inherent resilient "bendiness" due to material properties, although such objects are not considered "flexible" as the term is used herein. A flexible part may have infinite degrees of freedom (DOF's). Examples of such parts include closed, bendable tubes (made from, e.g., NITINOL, polymer, soft rubber, and the like), helical coil springs, etc. that can be bent into various simple or compound curves, often without significant cross-sectional deformation. Other flexible parts may approximate such an infinite-DOF part by using a series of closely spaced components that are similar to a snake-like arrangement of serial "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible part may serve as, and be modeled as, a single mechanical constraint (joint) that provides one or more DOF's between two links in a kinematic chain, even though the flexible part itself may be a kinematic chain made of several coupled links. Knowledgeable persons will understand that a part's flexibility may be expressed in terms of its stiffness.

Unless otherwise stated in this description, a flexible part, such as a mechanical structure, component, or component assembly, may be either actively or passively flexible. An actively flexible part may be bent by using forces inherently associated with the part itself. For example, one or more tendons may be routed lengthwise along the part and offset from the part's longitudinal axis, so that tension on the one or more tendons causes the part or a portion of the part to bend. Other ways of actively bending an actively flexible part include, without limitation, the use of pneumatic or hydraulic power, gears, electroactive polymer (more generally, "artificial muscle"), and the like. A passively flexible part is bent by using a force external to the part (e.g., an applied mechanical or electromagnetic force). A passively flexible part may remain in its bent shape until bent again, or it may have an inherent characteristic that tends to restore the part to an original shape. An example of a passively flexible part with inherent stiffness is a plastic rod or a resilient rubber tube. An actively flexible part, when not actuated by its inherently associated forces, may be passively flexible. A single part may be made of one or more actively and passively flexible parts in series.

Aspects of the invention are described primarily in terms of an implementation using a da Vinci® Surgical System, commercialized by Intuitive Surgical, Inc. of Sunnyvale, California. Examples of such surgical systems are the da Vinci® Xi™ Surgical System (Model IS4000) and the da Vinci® Si™ HD™ Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely exemplary and are not to be considered as limiting the scope of the inventive aspects disclosed herein. As applicable, inventive aspects may be embodied and implemented in both relatively smaller, hand-held, hand-operated devices and relatively larger systems that have additional mechanical support.

It should be understood that the diminutive scale of the disclosed structures and mechanisms creates unique mechanical conditions and difficulties with the construction of these structures and mechanisms that are unlike those found in similar structures and mechanisms constructed at a larger scale, because forces and strengths of materials do not scale at the same rate as the size of the mechanisms. For example, a surgical instrument having an 8 mm shaft diameter cannot simply be scaled down to a 5 mm shaft diameter due to mechanical, material property, and manufacturing considerations. Likewise, a 5 mm shaft diameter device cannot simply be scaled down to a 3 mm shaft diameter device. Significant mechanical concerns exist as physical dimensions are reduced.

A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller", encompasses both single-location and distributed implementations.

This disclosure provides improved surgical and robotic devices, systems, and methods. The inventive concepts are particularly advantageous for use with surgical robotic systems in which a plurality of surgical tools or instruments will be mounted on and moved by an associated plurality of robotic manipulators during a surgical procedure. The robotic systems will often comprise tele-robotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site. "Linkage" is used in this application to indicate a single link, and to indicate a system comprising multiple links (and one or more joints), as applicable. The large number of degrees of freedom may also allow a processor to position the manipulators to inhibit interference or collisions between these moving structures, and the like.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector that is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base that is fixed in space during at least a portion of a robotic procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both.

When used for minimally invasive robotic surgery, movement of the manipulator assembly may be controlled by one or more processors (or simply "a processor") of the system so that a shaft or intermediate portion of the tool or instrument is constrained to a safe motion through a minimally invasive surgical access site or other aperture. Such motion may include, for example, axial insertion of the shaft through the aperture site, rotation of the shaft about its axis, and pivotal motion of the shaft about a pivot point adjacent the access site, but will often preclude excessive lateral motion of the shaft which might otherwise tear the tissues adjacent the aperture or enlarge the access site inadvertently. Some or all of such constraint on the manipulator motion at the access site may be imposed using mechanical manipulator joint linkages that inhibit improper motions, or may in part or in full be imposed using robotic data processing and control techniques. Hence, such minimally invasive aperture-constrained motion of the manipulator assembly may employ between zero and three degrees of freedom of the manipulator assembly.

Many of the exemplary manipulator assemblies described herein will have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom-three for location, and three for orientation-plus three degrees of freedom to comply with the access site constraints), but will often have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly. It should be noted that any degree of freedom that is actively position-controlled could potentially be controlled using force control, or impedance control, or admittance control, or any combination of the forgoing.

Referring to FIGS. 1 and 2, computer-assisted surgery systems for minimally invasive telesurgery (or "computer-assisted robotic systems") can include a patient-side cart 100 and an operator console such as a surgeon console 40. Telesurgery is a general term for surgical systems where the surgeon uses some form of remote control, e.g., a servo-mechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient, avoiding the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120 (or "manipulator assembly 120"), a second robotic manipulator arm assembly 130 (or "manipulator assembly 130"), a third robotic manipulator arm assembly 140 (or "manipulator assembly 140"), and a fourth robotic manipulator arm assembly 150 (or "manipulator assembly 150"). Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment the base 110 includes casters to allow case of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that another instrument may be introduced at the work site. Alternatively, the remaining robotic manipulator arm assembly may be used for introducing a second endoscope or another image capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot occurs at its entry aperture into the patient. The device manipulator may then manipulate its held device so that it may be pivoted about the pivot, inserted into and retracted out of the entry aperture, and rotated about its shaft axis. The pivot may be also be referred to as the "pivot point" in this disclosure, since pivoting motion about a pivot can be ideally modeled and explained as rotational motion about a specific point in space. Also, in some embodiments, the "pivot" or "pivot point" may be implemented as a point; the resulting pivoting motion about the "pivot" or "pivot point" then involves no translation of the center of rotation (or the minimum amount of translation of the center possible given the design of the system). However, in various embodiments, the "pivot" or "pivot point" may be implemented as a set of points within specified boundaries, a small portion of space, or the like. The resulting pivoting motion about the "pivot" or "pivot point" may then include limited translation of the center of rotation, while the overall motion is still substantially about a center of rotation. The amount of translational motion can vary. For example, in some embodiments, the amount of translational motion is imperceptible to average humans with un-augmented senses. As another example, in some embodiments, the amount of translational motion is similar to what may be found in mechanical pivot joints.

In the depicted embodiment, the surgeon console 40 includes a stereo vision display 45 so that the user may view the surgical work site in stereo vision from images captured by the stereoscopic camera of the patient-side cart 100. Left and right eyepieces, 46 and 47, are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control, using the processor(s) of the surgery system, the motion of robotic instruments.

The surgeon console 40 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six degrees-of-freedom ("DOF"). Foot pedals 44 with toe and heel controls are provided on the surgeon console 40 so the user may control movement and/or actuation of devices associated with the foot pedals.

A processor 43 is provided in the surgeon console 40 for control and other purposes. The processor 43 performs various functions in the medical robotic system. One function performed by processor 43 is to translate and transfer the mechanical motion of input devices 41, 42 to actuate their respective joints in their associated robotic manipulator arm assemblies 120, 130, 140, and 150 so that the surgeon can effectively manipulate devices, such as the surgical instruments. Another function of the processor 43 is to implement the methods, cross-coupling control logic, and controllers described herein.

Although a surgeon console 40 is described in the example above, it is to be appreciated that the operator console may be a console not designed with the surgeon as the primary user. For example, the operator console may be designed for another member of the surgical team (anesthesiologist, assistant, etc.) as the primary user, for use by the surgeon with other member(s) of the surgical team at the same or different times, or for general use by any member of the surgical team. Also, in other embodiments, the operator console may be designed for non-surgical medical uses, or for non-medical uses.

Although described as a processor, it is to be appreciated that the processor 43 (and other "processors" described herein) may be implemented by any combination of hardware, software and firmware. Also, its functions as described herein may be performed by one unit or divided up among a number of subunits, each of which may be implemented in turn by any combination of hardware, software and firmware. Further, although being shown as part of or being physically adjacent to the surgeon console 40, the processor 43 may also be distributed as subunits throughout the telesurgery system.

The processor 43 (and the processors of the other surgery systems described herein) can execute machine-readable instructions from non-transitory machine-readable media that activate the processor 43 to perform actions corresponding to the instructions. Accordingly, it should be understood that the disclosure of computer-assisted surgery techniques and methods herein includes a concomitant disclosure of non-transitory machine-readable media comprising corresponding machine-readable instructions.

Figure 3:
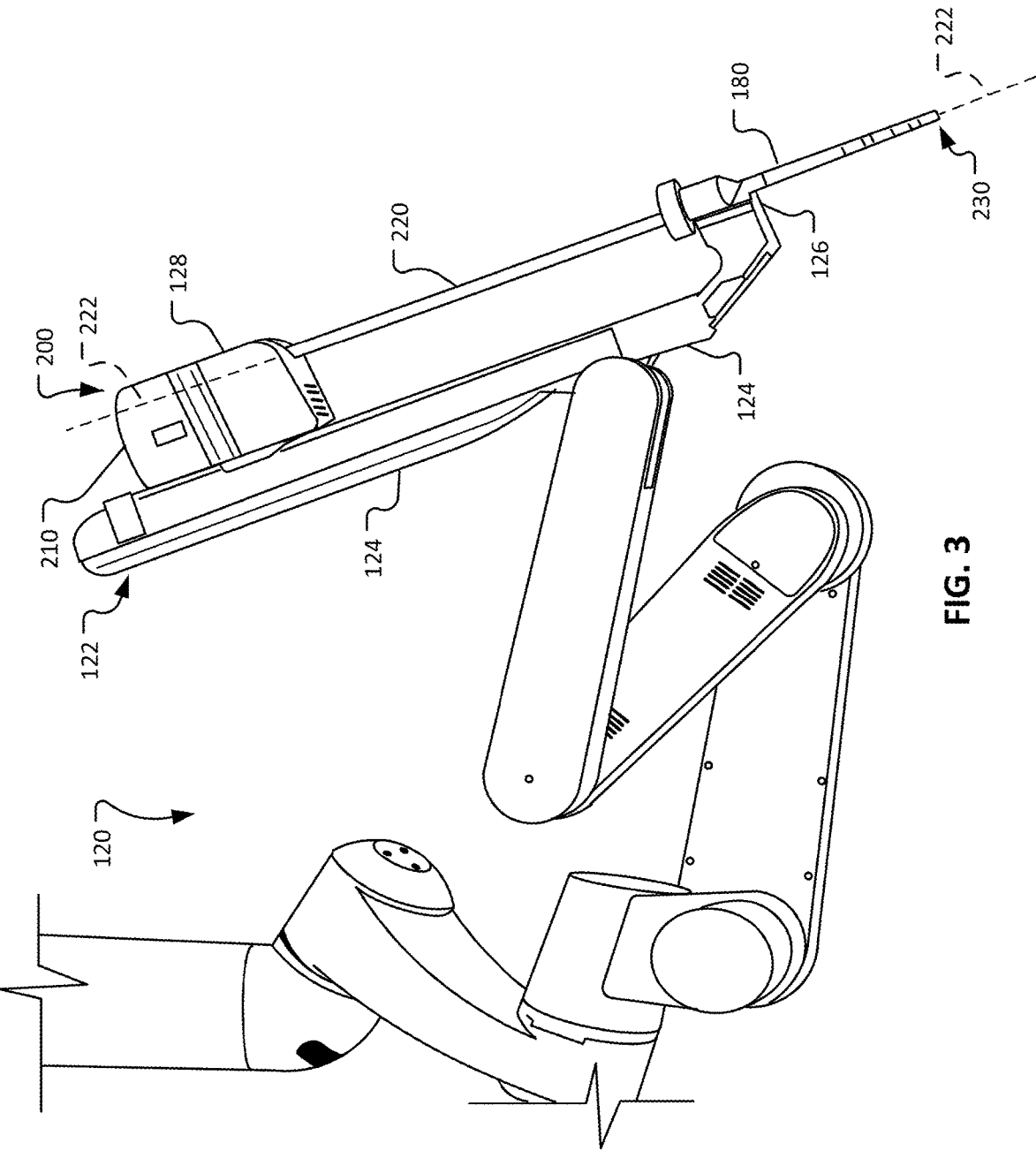
FIG. 3 is a side view of an example robotic manipulator arm assembly of a computer-assisted tele-operated surgery system.

Referring also to FIG. 3, the robotic manipulator arm assemblies 120, 130, 140, and 150 can manipulate devices such as surgical instruments to perform minimally invasive surgery. For example, in the depicted arrangement the robotic manipulator arm assembly 120 is pivotably coupled to an instrument holder 122. A cannula 180 and a surgical instrument 200 and are, in turn, releasably coupled to the instrument holder 122. The cannula 180 is a tubular member that is located at the patient interface site during a surgery. The cannula 180 defines a lumen in which an elongate shaft 220 of the surgical instrument 200 is slidably disposed. In some embodiments, a processor of the surgery systems described herein is configured to detect a releasable coupling of the cannula 180 to the manipulator assembly 120, for example.

The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable by the surgeon console 40 and processor 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processor 43.

The surgical instrument 200 includes a transmission assembly 210, the elongate shaft 220, and an end effector 230. The transmission assembly 210 is releasably couplable with the instrument holder carriage 128. The shaft 220 extends distally from the transmission assembly 210. The end effector 230 is disposed at a distal end of the shaft 220. In some embodiments, a processor of the surgery systems described herein is configured to detect an installation of the surgical instrument 200 to the manipulator assembly 120, for example.

The shaft 220 defines a longitudinal axis 222 that is coincident with a longitudinal axis of the cannula 180, and is coincident with a longitudinal axis of the lumen defined by the cannula 180. As the instrument holder carriage 128 translates along the instrument holder frame 124, the elongate shaft 220 of the surgical instrument 200 is moved along the longitudinal axis 222. In such a manner, the end effector 230 can be inserted and/or retracted from a surgical workspace within the body of a patient.

Figure 4:
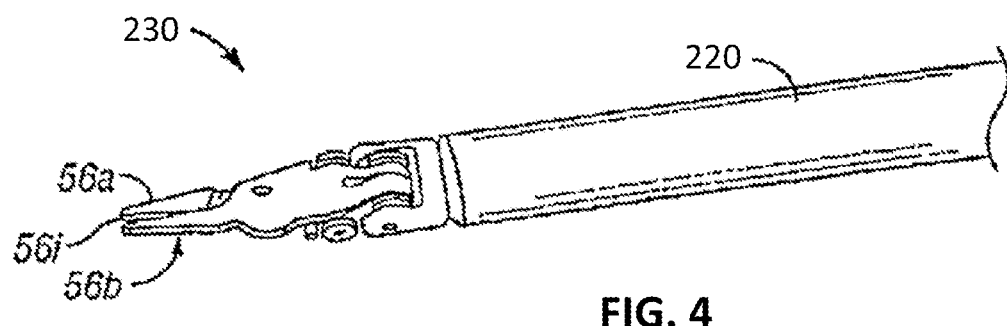
FIG. 4 is a perspective view of a distal end portion of an example surgical instrument in a first configuration.
Figure 5:
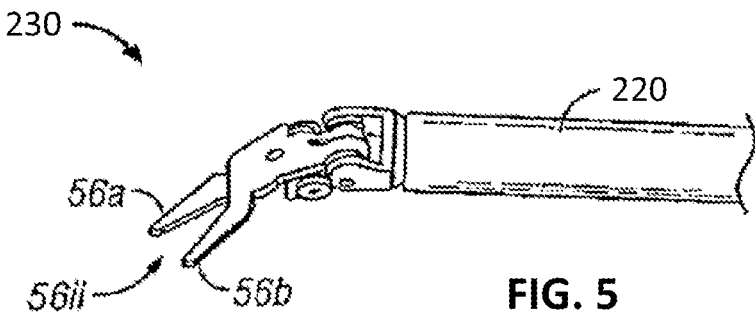
FIG. 5 is a perspective view of the distal end portion of the surgical instrument of FIG. 4 in a second configuration.
Figure 6:
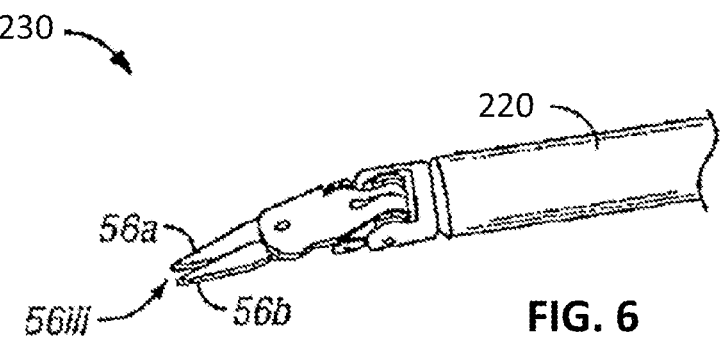
FIG. 6 is a perspective view of the distal end portion of the surgical instrument of FIG. 4 in a third configuration.

Also referring to FIGS. 4-6, a variety of alternative robotic surgical instruments of different types and differing end effectors 230 may be used, with the instruments of at least some of the manipulators being removed and replaced during a surgical procedure. Several of these end effectors, including, for example, DeBakey Forceps 56*i*, microforceps 56*ii*, and Potts scissors 56*iii* include first and second end effector elements 56*a*, 56*b* which pivot relative to each other so as to define a pair of end effector jaws. Other end effectors, including scalpels and electrocautery probes, have a single end effector element. For instruments having end effector jaws, the jaws will often be actuated by squeezing the grip members of input devices 41, 42.

The elongate shaft 220 allow the end effector 230 and the distal end of the shaft 220 to be inserted distally into a surgical worksite through a minimally invasive aperture (here, via cannula 180), often through an abdominal wall or the like. The surgical worksite may be insufflated, and movement of the end effectors 230 within the patient will often be effected, at least in part, by pivoting of the instruments 200 about the location at which the shaft 220 passes through the minimally invasive aperture. In other words, the robotic manipulator arm assemblies 120, 130, 140, and 150 will move the transmission assembly 210 outside the patient so that the shaft 220 extends through a minimally invasive aperture location so as to help provide a desired movement of end effector 50. Hence, the robotic manipulator arm assemblies 120, 130, 140, and 150 will often undergo significant movement outside patient during a surgical procedure.

Referring to FIGS. 7-10, an example robotic manipulator arm assembly 304 can be coupled with a surgical instrument 306 to affect movements of the instrument 306 relative to a base 302. As a number of different surgical instruments having differing end effectors may be sequentially mounted on each robotic manipulator arm assembly 304 during a surgical procedure (typically with the help of a surgical assistant), an instrument holder 320 will preferably allow rapid removal and replacement of the mounted surgical instrument 306. It should be understood that the example robotic manipulator arm assembly 304 is merely one non-limiting example of a variety of types of robotic manipulator arm assemblies envisioned within the scope of this disclosure.

The example robotic manipulator arm assembly 304 is mounted to the base 302 by a pivotal mounting joint 322 so as to allow the remainder of robotic manipulator arm assembly 304 to rotate about a first joint axis J1, with the first joint 322 providing rotation about a vertical axis in the exemplary embodiment. Base 302 and first joint 322 generally comprise a proximal portion of robotic manipulator arm assembly 304, with the manipulator extending distally from the base toward instrument holder 320 and end effector 50.

Figure 7:
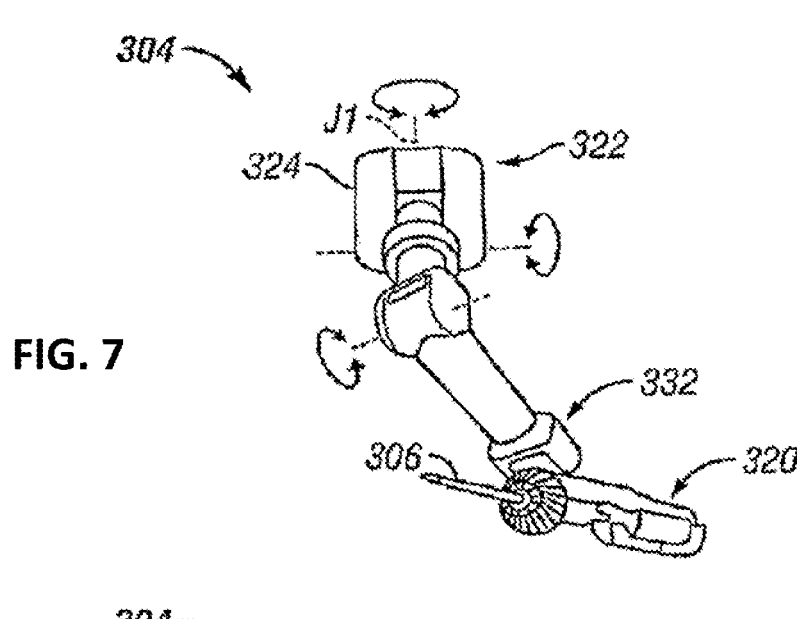
FIGS. 7-9 are bottom, side, and back views of an exemplary robotic manipulator assembly having a range of joint states for a given end effector position.
Figure 8:
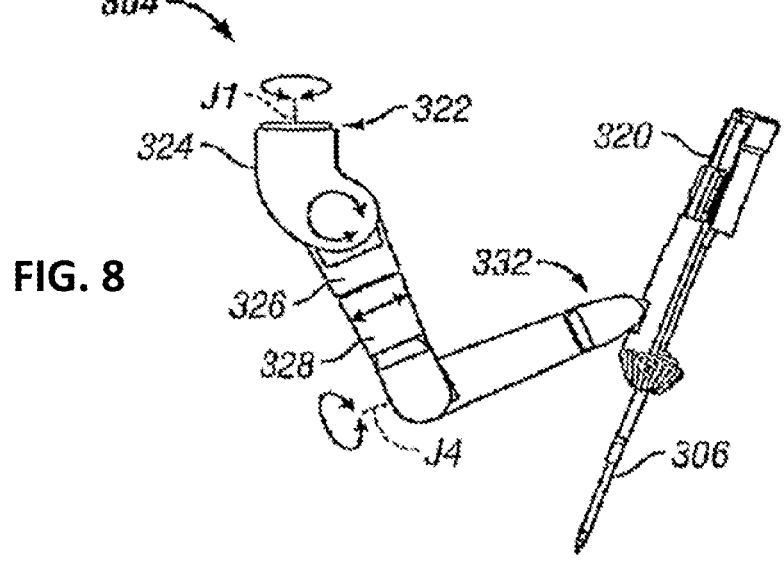
Figure 9:
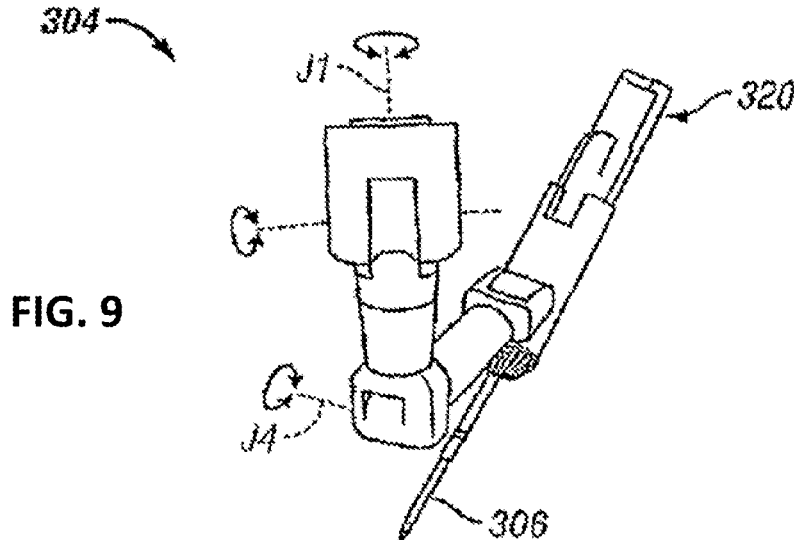
Figure 10:
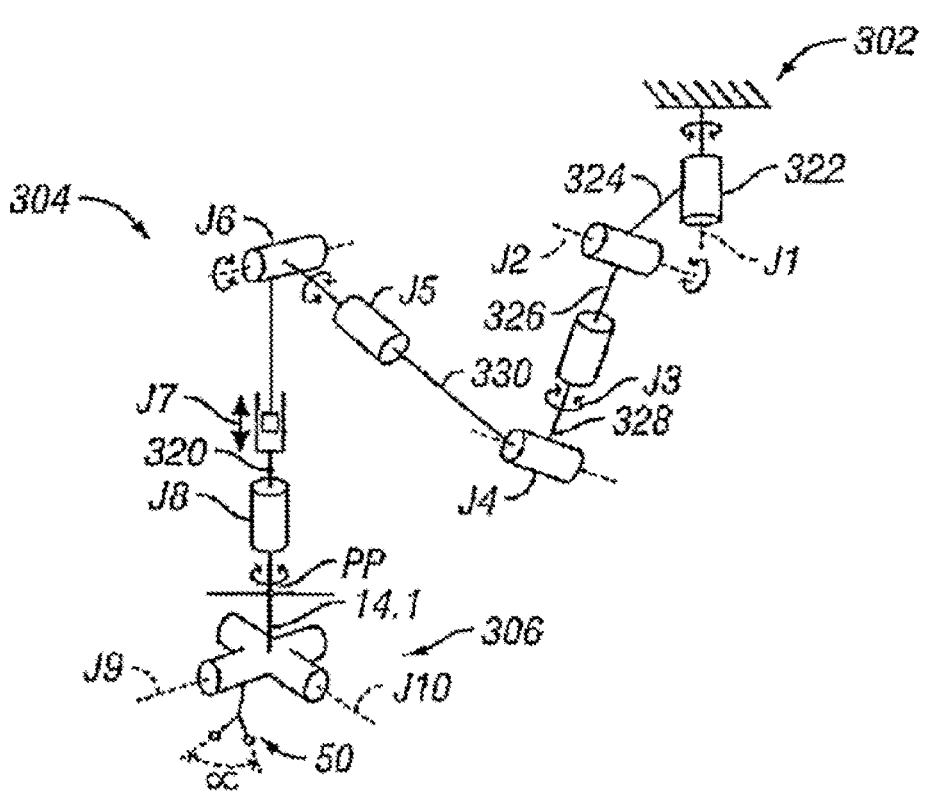
FIG. 10 is a schematic diagram illustrating the degrees of freedom provided by the robotic manipulator assembly of FIGS. 7-9.

Describing the individual links of the robotic manipulator arm assembly 304 as illustrated in FIGS. 7-9, along with the axes of rotation of the joints connecting the links as illustrated in FIG. 10, a first link 324 extends distally from base 302 and rotates about first pivotal joint axis J1 at joint 322. Many of the remainder of the joints can be identified by their associated rotational axes in FIG. 10. For example, a distal end of first link 324 is coupled to a proximal end of a second link 326 at a joint providing a horizontal pivotal axis J2. A proximal end of a third link 328 is coupled to the distal end of the second link 326 at a roll joint so that the third link generally rotates or rolls at joint J3 about an axis extending along (and ideally aligned with) axes of both the second and third links. Proceeding distally, after another pivotal joint J4, the distal end of a fourth link 330 is coupled to instrument holder 320 by a pair of pivotal joints J5, J6 that together define an instrument holder wrist 332. A translational or prismatic joint J7 of the robotic manipulator arm assembly 304 facilitates axial movement of instrument 306 through the minimally invasive aperture, and also facilitates attachment of the instrument holder 320 to a cannula through which the instrument 306 is slidably inserted.

Distally of instrument holder 320, the surgical instrument 306 may include additional degrees of freedom. Actuation of the degrees of freedom of the surgical instrument 306 will often be driven by motors of the robotic manipulator arm assembly 304. Alternative embodiments may separate the surgical instrument 306 from the supporting manipulator arm structure at a quickly detachable instrument holder/instrument interface so that one or more joints shown here as being on the surgical instrument 306 are instead on the interface, or vice versa. In other words, the interface between the surgical instrument 306 and robotic manipulator arm assembly 304 may be disposed more proximally or distally along the kinematic chain of the manipulator arm assembly 304 (which may include both the surgical instrument and the manipulator arm assembly 304). In the exemplary embodiment, the surgical instrument 306 includes a rotational joint J8 proximally of the pivot point PP, which generally is disposed at the site of a minimally invasive aperture. A distal wrist of the surgical instrument 306 allows pivotal motion of end effector 50 about instrument wrist joint axes J9, J10. An angle α between end effector jaw elements may be controlled independently of the end effector 50 location and orientation.

Figure 11:
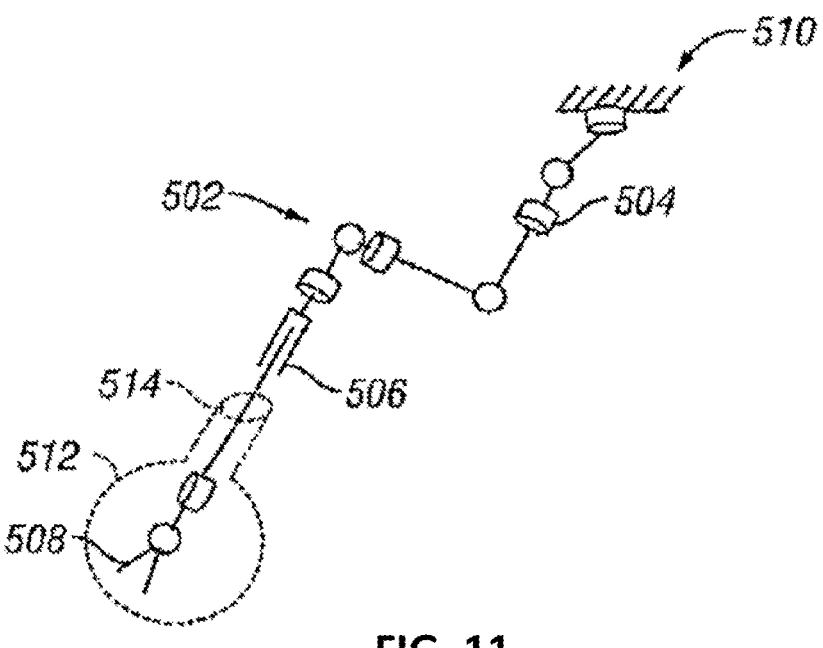
FIG. 11 is a schematic diagram illustrating a robotic manipulator assembly inserted through a surgical aperture.
Figure 12:
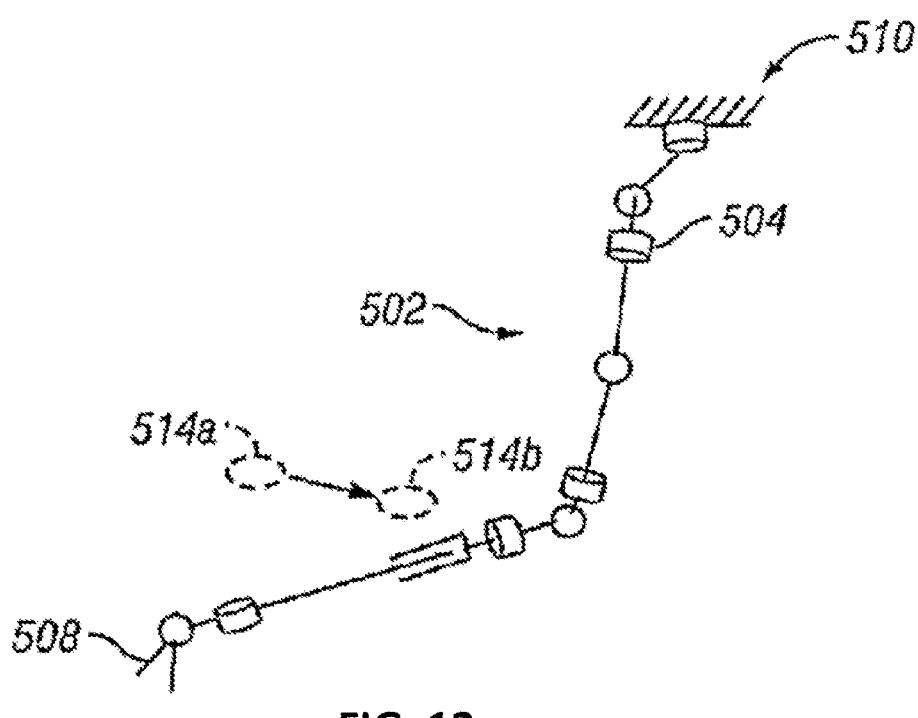
FIG. 12 schematically illustrates some of the challenges in manually repositioning the highly configurable manipulator assembly of FIG. 11 to a new aperture position.
Figure 13:
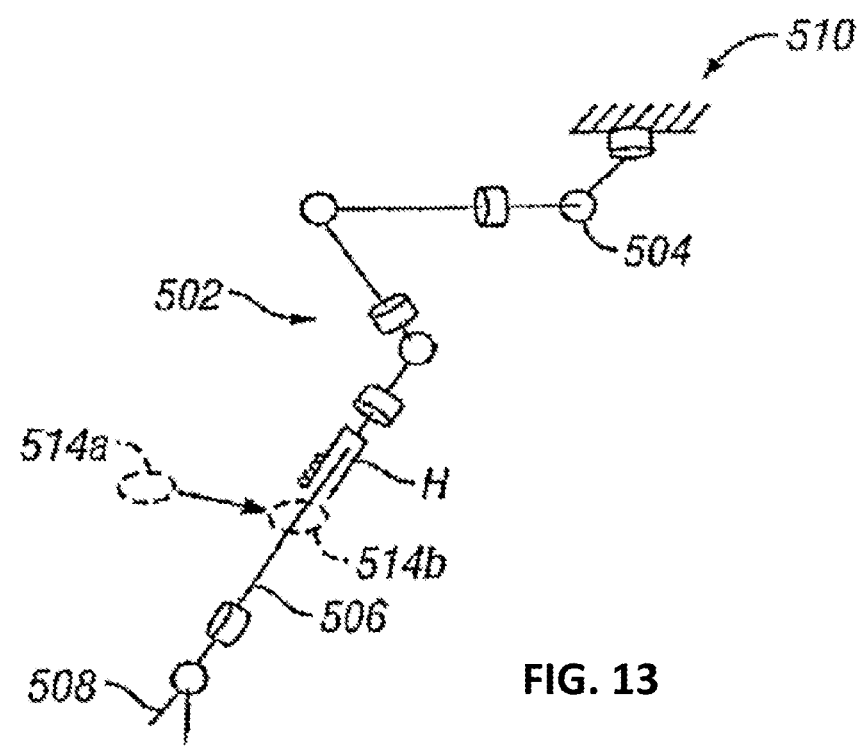
FIG. 13 schematically illustrates reconfiguring of the arm of FIG. 11 to enhance range of motion or the like during manual repositioning of the manipulator to a new aperture position.

Referring now to FIGS. 11-13, an example robotic manipulator arm assembly 502 includes a manipulator arm 504 (also "manipulator arm assembly 504") and a surgical instrument 506 having an end effector 508. The term manipulator assembly, as used herein, may in some cases also encompass the manipulator arm without the surgical instrument mounted thereon. The illustrated robotic manipulator arm assembly 502 generally extends from a proximal base 510 distally to the end effector 508, with the end effector 508 and distal portion of the surgical instrument 506 configured for insertion into an internal surgical site 512 via a minimally invasive aperture 514 allowing access to the surgical site 512. The joint structure of the robotic manipulator arm assembly 502 is similar to that described above regarding FIG. 10, and includes sufficient degrees of freedom to allow the manipulator assembly to be anywhere within a range of differing joint states for a given end effector position, even when the surgical instrument 506 is constrained to passage through minimally invasive aperture 514.

When the access site to a minimally invasive surgical procedure is to be changed from a first aperture location 514a to a second aperture location 514b, it will often be desirable to manually reposition some or all of the links of the robotic manipulator arm assembly 502. Similarly, when initially setting up the robotic manipulator assembly 502 for surgery, the manipulator assembly 502 may be manually moved into a desired position aligned with the aperture location through which the associated surgical instrument 506 is to access the surgical site 512. However, in light of the highly configurable manipulator arm structure having a relatively large number of joints between (for example) base 510 and the instrument/manipulator interface (see FIG. 10), such manual positioning of the links can be challenging. Even when the robotic manipulator assembly 502 structure is balanced to avoid gravitational effects, attempting to align each of the joints in an appropriate arrangement can be difficult for one person, time consuming, and may involve significant training and/or skill. The challenges can be even greater when the links of the robotic manipulator assembly 502 are not balanced about the joints, as positioning such a highly configurable structures in an appropriate configuration to begin surgery can be a struggle due to the manipulator's arm length and its passive and limp design.

To facilitate setting up the robotic manipulator assembly 502 for a surgical procedure (or to facilitate reconfiguring the manipulator assembly 502 for accessing a different tissue of the patient), the processor 43 of surgeon console 40 (see FIG. 2) may actively drive joints of the manipulator assembly during 502. In some cases, such driving may be in response to manual movement of at least one joint of the manipulator assembly 502. In FIG. 13, a hand H of a system operator (optionally a surgeon, assistant, technician, or the like) manually moves a link of the robotic manipulator arm assembly 502 or the surgical instrument 506 into alignment with a desired minimally invasive aperture location 514b. During this movement, the processor drives joints proximal of the hand/manipulator engagement. As the robotic manipulator arm assembly 502 will often have sufficient degrees of freedom so as to be in a range of alternative configurations, the proximal joints may be driven to a desired manipulator state without inhibiting the manual positioning of the distal portion of the robotic manipulator arm assembly 502. Optionally, the joints may be driven so as to compensate for gravity, to inhibit momentum effects, to provide a desired (and often readily overcome) resistance to the manual movement so as to give the hand the impression of plastically deforming the manipulator structure at its joints, so as to keep the configurable linkage assembly in a desired pose, or the like. While this movement is shown in FIG. 13 as being performed with the surgical instrument 506 attached to the robotic manipulator arm assembly 504, the manipulator assembly will often be manually positioned prior to attachment of the surgical instrument 506 to the robotic manipulator arm assembly 504.

Figure 14:
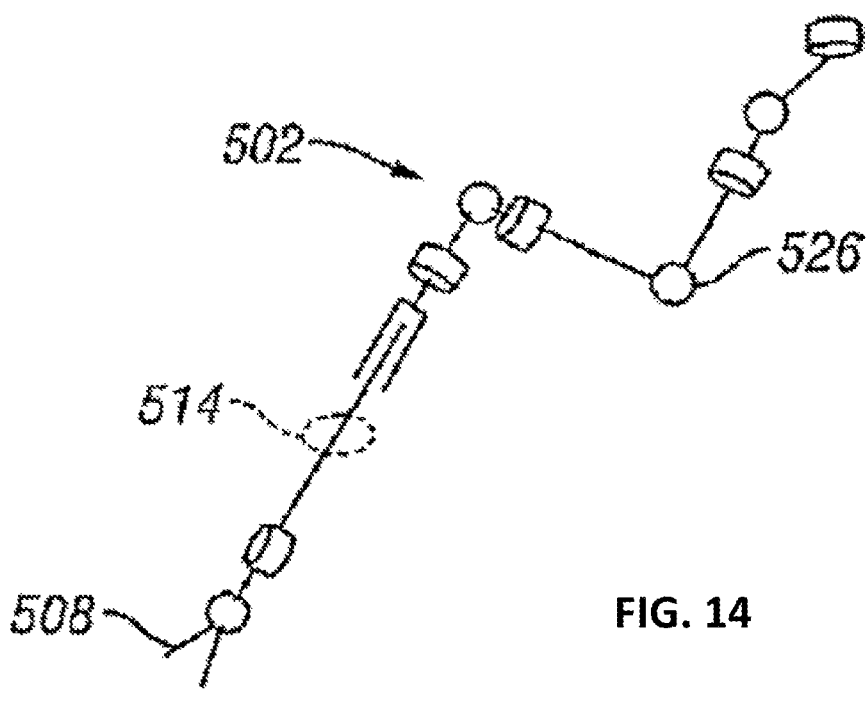
FIGS. 14 and 15 schematically illustrate robotically reconfiguring of the joints of the manipulator assembly within a range of alternative joint configurations during manual movement of the arm.
Figure 15:
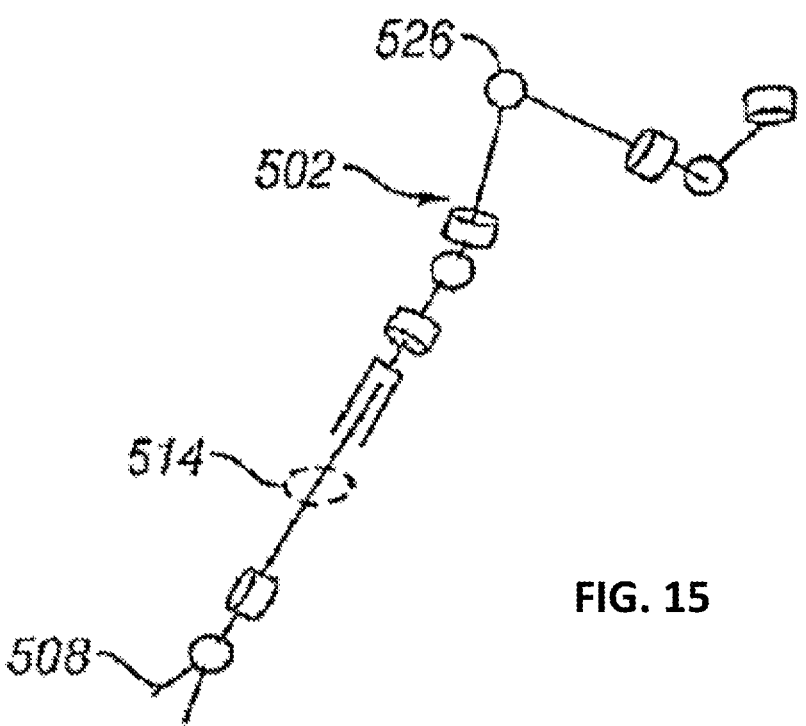

Referring to FIGS. 14 and 15, the robotic manipulator assembly 502 may be reconfigured by the processor 43 (FIG. 2) for any of a variety of differing reasons. For example, a joint 526 may be driven from a downward oriented apex configuration to an upward oriented apex configuration so as to inhibit collisions with an adjacent arm, equipment, or personnel; to enhance a range of motion of the end effector 508; in response to physiological movement of the patient such as patient breathing or the like; in response to repositioning of the patient, such as by reorienting a surgical table; and the like. Some, but not all, of these changes in configuration of the robotic manipulator assembly 502 may be in response to external forces applied to the manipulator assembly 502, with the processor 43 often driving a different joint of the manipulator assembly 502 than that which is being acted upon by the external force. In other cases, the processor 43 will reconfigure the robotic manipulator assembly 502 in response to calculations performed by the processor 43. In either case, the processor 43 may vary from a simple master-slave controller to drive the robotic manipulator assembly 502 in response to a signal to provide a preferred manipulator assembly 502 configuration. Such configuring of the robotic manipulator assembly 502 may occur during master-slave end effector movements, during manual or other reconfiguration of the manipulator assembly 502, and/or at least in part at a different time, such as after releasing a clutch input.

Figure 16:
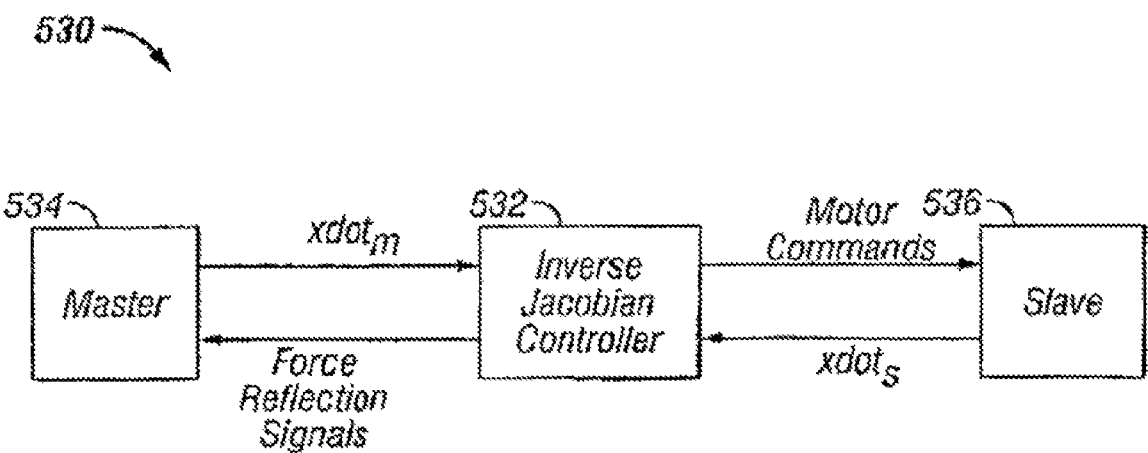
FIG. 16 is a simplified block diagram schematically illustrating a fully constrained inverse Jacobian master/slave velocity controller.

Referring now to FIG. 16, a simplified controller schematic diagram 530 shows a master/slave controller 532 coupling a master input device 534 to a slave manipulator 536. In this example, the controller inputs, outputs, and computations are described using vector mathematical notation in which the vector x will often refer to a position vector in a Cartesian coordinates, and in which the vector q will reference a joint articulation configuration vector of an associated linkage (most often of the manipulator slave linkage), sometimes referred to as the linkage position in joint space. Subscripts can be appended to these vectors to identify a specific structure when ambiguity might otherwise exist, so that $x_m$ (for example) is a position of the master input device in the associated master workspace or coordinate system, while $x_s$, indicates a position of the slave in the workspace. Velocity vectors associated with the position vectors are indicated by a dot over the vector or the word "dot" between the vector and the subscript, such as $x dot_m$ or $\dot{x}_m$ for the master velocity vector, with the velocity vectors being mathematically defined as the change in the position vector with a change in time ($dx_m/dt$ for the master velocity vector example).

Example controller 532 comprises an inverse Jacobian velocity controller. Where $x_m$ is a position of the master input device and $x_m$ is the velocity of the master input device, the controller 532 calculates motor commands for transmission to the slave manipulator 536 to effect slave end effector motions that correspond to the input device from the master velocities. Similarly, controller 532 can calculate force reflection signals to be applied to the master input device (and from there to the operator's hand) from the slave position $x_s$ and/or slave velocity $x_s$. A number of refinements to this simple master/slave inverse Jacobian controller schematic are desirable, including those illustrated in FIG. 19 and described in detail in U.S. Pat. No. 6,424,885 ("the '885 patent"), the full disclosure of which is incorporated herein by reference.

Figure 17:
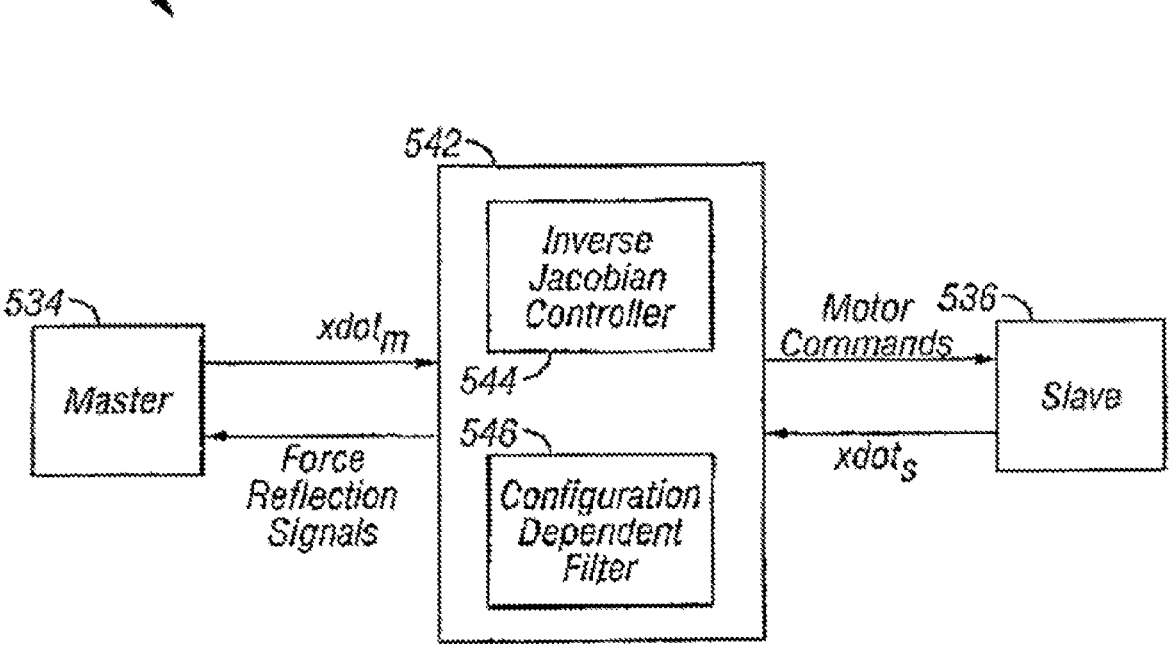
FIG. 17 is a simplified diagram of a modified master/slave controller in which an inverse Jacobian controller module is combined with a second module having a configuration dependent subspace filter to allow control over a manipulator assembly.

Referring now to FIG. 17, a processor 542 (also "controller 542") may be characterized as including a first controller module 544 (also "first module 544") and a second controller module 546 (also "second module 546"). The first module 544 may comprise a primary joint controller, such as an inverse Jacobian master-slave controller. The primary joint controller of first module 544 may be configured for generating the desired manipulator assembly movements in response to inputs from the master input device 534. However, as noted above, many of the manipulator linkages described herein have a range of alternative configurations for a given end effector position in space. As a result, a command for the end effector to assume a given position could result in a wide variety of different joint movements and configurations, some of which may be much more desirable than others. Hence, the second module 546 may be configured to help drive the manipulator assembly to a desired configuration, in some embodiments driving the manipulator toward a preferred configuration during master-slave movements. In many embodiments, second module 546 will comprise a configuration dependent filter.

In broad mathematical terms, both the primary joint controller of first module 544 and the configuration dependent filter of second module 546 may comprise filters used by processor 542 to route control authority for linear combinations of joints to the service of one or more surgical goals or tasks. If we assume that X is the space of joint motion, F(X) might be a filter giving control over the joints to i) provide a desired end effector movement, and ii) provide pivotal motion of the instrument shaft at the aperture site. Hence, the primary joint controller of first module 544 may comprise filter F(X). Conceptually, $(1-F^{-1}F)(X)$ could describe a configuration dependent subspace filter giving control actuation authority to the linear combination of joint velocities that are orthogonal to serving the goal of the primary joint controller (in this example, end effector movement and pivotal instrument shaft motion). Hence, this configuration dependent filter could be used by the second module 546 of controller 542 to service a second goal, such as maintaining a desired pose of the manipulator assembly, inhibiting collisions, or the like. Both filters may be further sub-divided into more filters corresponding to serving more specific tasks. For example, filter F(X) could be separated into $F_1(X)$ and $F_2(X)$ for control of the end effector and control of the pivotal shaft motion, respectively, either of which may be chosen as the primary or highest priority task of the processor.

While the mathematical calculations performed by the modules may (at least in part) be similar, the robotic processors and control techniques described herein will often make use of a primary joint controller configured for a first (sometimes referred to as a primary) controller task, and a configuration dependent filter which makes use of an under-constrained solution generated by the primary joint controller for a second (also referred to as secondary) task. In much of the following description, the primary joint controller will be described with reference to a first module, while the configuration dependent filter will be described with reference to a second module. Additional functions (such as additional subspace filters) and or additional modules of varying priorities may also be included.

As noted elsewhere herein, the hardware and/or programming code for performing the functions described with reference to such first and second modules may be fully integrated, partially integrated, or fully separate. Controller 542 may employ the functions of the two modules simultaneously, and/or may have a plurality of differing modes in which one or both modules are used separately or in different ways. For example, in some embodiments, first module 544 might be used with little or no influence from second module 546 during master-slave manipulations, and the second module 546 having a greater role during setup of the system when the end effector is not being driven robotically, such as during port clutching or other manual articulations of the manipulator assembly. Nonetheless, in many embodiments both modules may be active most of or all the time robotic motion is enabled. For example, by setting gains of the first module to zero, by setting $x_s$ to $x_{s, actual}$, and/or by reducing the matrix rank in the inverse Jacobian controller so that it doesn't control as much and letting the configuration dependent filter have more control authority, the influence of the first module on the state of the manipulator assembly can be reduced or eliminated so as to change a mode of processor 542 from a tissue manipulator mode to a clutch mode.

Figure 18:
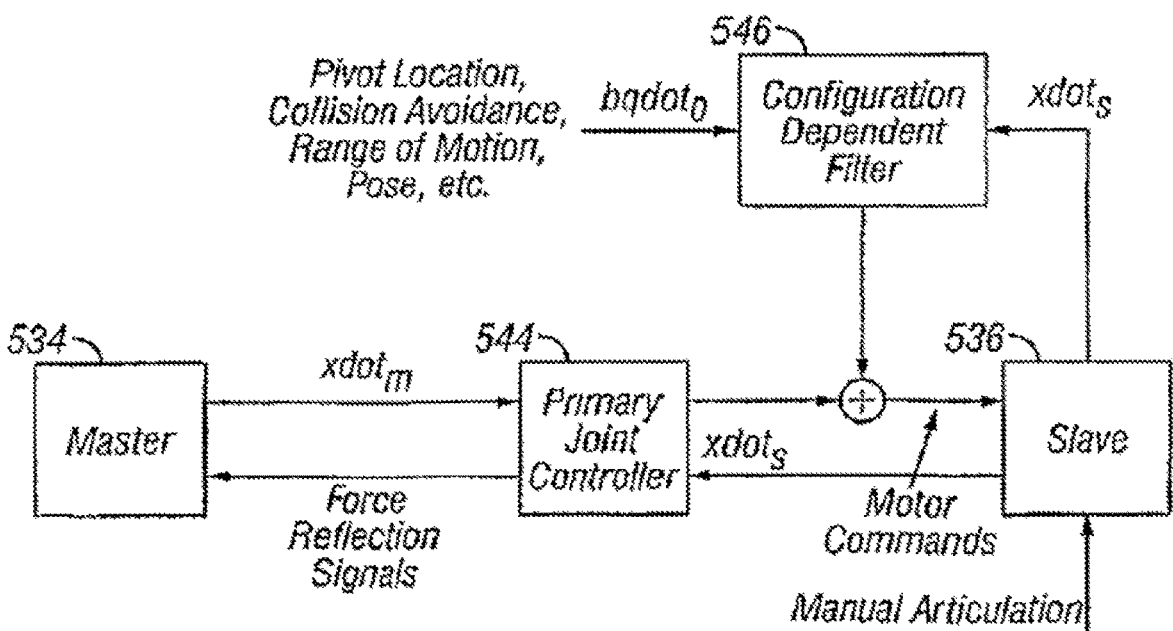
FIG. 18 illustrates a refinement of the simplified master-slave control illustrated in FIG. 17.

FIG. 18 illustrates a refinement of the simplified master-slave control schematic 540 from FIG. 17, and shows how different modules might be used in different processor modes. As illustrated in FIG. 18, first module 544 may, for example, comprise some form of a Jacobian controller having a Jacobian-related matrix. Second module 546 may, in a port clutch mode, receive signals from the slave manipulator 536 indicating a position or velocity of the slave generated at least in part by manual articulation of the slave manipulator linkage. In response to this input, the second module 546 can generate motor commands appropriate for driving the joints of the slave so as to allow the manual articulation of the slave linkage while configuring the slave in the desired joint configuration. During master-slave end effector manipulation, the controller may use second module 546 to help derive motor commands based on a different signal $bqdot_0$. This alternative input signal to the second module 546 of controller 542 may be used to drive the manipulator linkage so as to maintain or move the minimally invasive aperture pivot location along the manipulator structure, so as to avoid collisions between a plurality of manipulators, so as to enhance a range of motion of the manipulator structure and/or avoid singularities, so as to produce a desired pose of the manipulator, or the like. In some embodiments, the alternative input signal to the second module is used to drive the manipulator linkage so as to maintain, or to move, the minimally invasive aperture pivot location in a prescribed way, while accounting for one or more other constraints on the motion of the manipulator linkage. Examples constraints include static or dynamic limits on the position, velocity, acceleration, jerk, or any combination of the foregoing for one or more parts of the manipulator linkage. Additional example constraints include static or dynamic limits on current draw, output power, output torque, output force, sensed torque or force, etc. Hence, $bqdot_0$ can generally comprise and/or indicate (for example) a desired set of joint velocities, more generally representing a secondary control goal, typically in joint space. In other embodiments, the processor may include separate modules and/or dependent configuration filters for clutching, secondary controller tasks, and the like.

Figure 20:
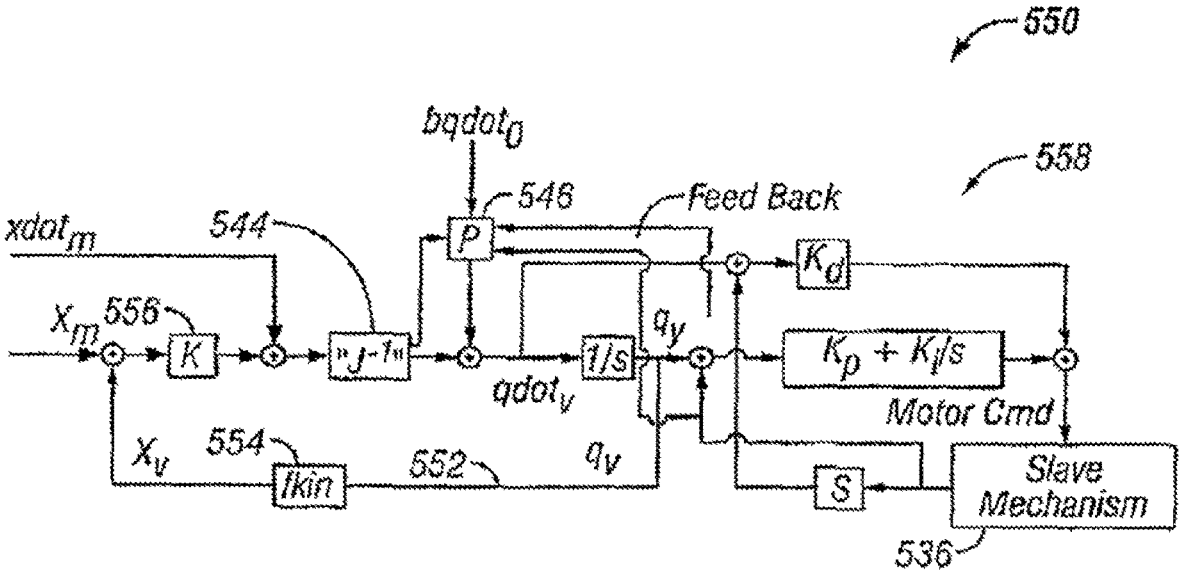
FIG. 20 schematically illustrates a modified portion of the controller of FIG. 11, in which the inverse Jacobian controller has been modified with a configuration dependent filter so that the controller respects priority of differing levels of system constraints and/or goals.
Figure 19:
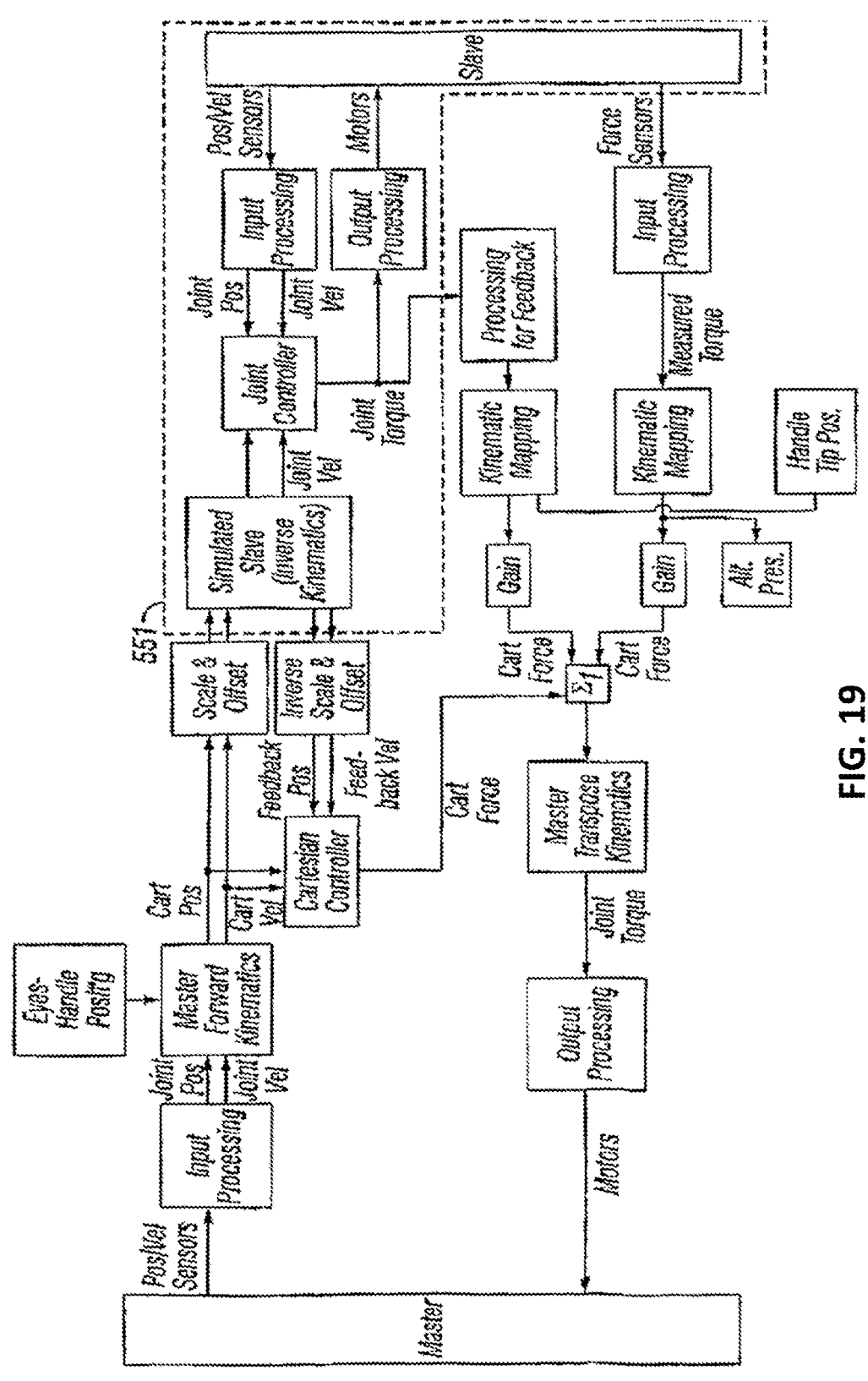
FIG. 19 schematically illustrates an exemplary inverse Jacobian controller for a fully constrained master/slave robotic surgical system.

Referring now to FIG. 20, a partial control schematic 550 illustrates modifications of the controller illustrated in FIG. 19. Control schematic 550 very roughly represents a modification of portion 551 of the controller of FIG. 11 to facilitate control over manipulator assemblies have large numbers of degrees of freedom. In the embodiment illustrated in FIG. 20, the first module 544 comprises an inverse Jacobian velocity controller, with the output from calculations made using an inverse Jacobian matrix modified according to a virtual slave path 552. First describing the virtual slave path, vectors associated with the virtual slave are generally indicated by a v subscript, so that a virtual slave velocity in joint space $qdot_v$ is integrated to provide $q_v$, which is processed using an inverse kinematic module 554 to generate a virtual slave joint position signal $x_v$. The virtual slave position and master input command $x_m$ are combined and processed using forward kinematics 556. The use of a virtual slave (often having simplified dynamics) facilitates smooth control and force reflection when approaching hard limits of the system, when transgressing soft limits of the system, and the like, as can be more fully understood with reference to the '885 patent previously incorporated herein by reference. Similarly, calculation of motor commands such as joint torque signals or the like from joint controllers in response to the output from the inverse Jacobian matrix (as modified or augmented by the second module 546) via appropriate joint controllers, input and output processing, and the like are more fully described in the '885 patent.

Addressing the structure generally indicated by the first and second control modules 544, 546, and of the other components of control schematic 550 and other controllers described herein, these structures will often comprise data processing hardware, software, and/or firmware. Such structures will often include reprogrammable software, data, and the like, which may be embodied in machine-readable code and stored in a tangible medium for use by processor 43 of surgeon console 40 (see FIG. 2). The machine-readable code may be stored in a wide variety of different configurations, including random access memory, non-volatile memory, write-once memory, magnetic recording media, optical recording media, and the like. Signals embodying the code and/or data associated therewith may be transmitted by a wide variety of communication links, including the Internet, an intranet, an Ethernet, wireless communication networks and links, electrical signals and conductors, optical fibers and networks, and the like. Processor 43 may, as illustrated in FIG. 2, comprise one or more data processors of surgeon console 40, and/or may include localized data processing circuits of one or more of the manipulators, the instruments, a separate and/or remote processing structure or location, and the like, and the modules described herein may comprise (for example) a single common processor board, a plurality of separate boards, or one or more of the modules may be separated onto a plurality of boards, some of which also run some or all of the calculation of another module. Similarly, the software code of the modules may be written as a single integrated software code, the modules may each be separated into individual subroutines, or parts of the code of one module may be combined with some or all of the code of another module. Hence, the data and processing structures may include any of a wide variety of centralized or distributed data processing and/or programming architectures.

Addressing the output of the controller of FIG. 20 in more detail, the controller will often seek to solve for one particular manipulator joint configuration vector q for use in generating commands for these highly configurable slave manipulator mechanisms. As noted above, the manipulator linkages often have sufficient degrees of freedom so as to occupy a range of joint states for a given end effector state. Such structures may (but will often not) comprise linkages having true redundant degrees of freedom, that is, structures in which actuation of one joint may be directly replaced by a similar actuation of a different joint along the kinematic chain. Nonetheless, these structures are sometimes referred to as having excess, extra, or redundant degrees of freedom, with these terms (in the broad sense) generally encompassing kinematic chains in which (for example) intermediate links can move without changing the position (including both location and orientation) of an end effector.

When directing movement of highly configurable manipulators using the velocity controller of FIG. 20, the primary joint controller of the first module often seeks to determine or solve for a virtual joint velocity vector $qdot_v$ that can be used to drive the joints of slave manipulator 536 in such a way that the end effector will accurately follow the master command $x_m$. However, for slave mechanisms with redundant degrees of freedom, an inverse Jacobian Matrix generally does not fully define a joint vector solution. For example, the mapping from Cartesian command xdot to joint motion qdot in a system that can occupy a range of joint states for a given end effector state is a mapping of one-to-many. In other words, because the mechanism is redundant, there are a mathematically infinite number of solutions, represented by a subspace in which the inverse lives. The controller may embody this relationship using a Jacobian matrix that has more columns than rows, mapping a plurality of joint velocities into comparatively few Cartesian velocities. Our solution $J^{-1}\dot{x}$ will often seek to undo this collapsing of the degrees of freedom of the slave mechanism into Cartesian workspace.

Additional descriptions pertaining to using a processor configured by software instructions to calculate a software-constrained remote center of motion of the robotic manipulator arm assembly can be found in U.S. Pat. No. 8,004,229, which is hereby incorporated by reference in its entirety.

In short, the above descriptions (and the descriptions in U.S. Pat. No. 8,004,229) enable the pivot (remote center of motion) to be determined/estimated through software, hence the notion of a software-constrained remote center of motion. By having the capability to compute software pivot points, different modes characterized by the compliance or stiffness of the system can be selectively implemented. More particularly, different system modes over a range of pivot points/centers (i.e., ranging from one have a passive pivot point to one having a fixed/rigid pivot point) can be implemented after an estimate pivot point is computed. For example, in a fixed pivot implementation, the estimated pivot point can be compared to a desired pivot point to generate an error output which can be used to drive the instrument's pivot to the desired location. Conversely, in a passive pivot implementation, while the desired pivot location may not be an overriding objective, an estimated pivot point can be used for error detection and consequently safety because changes in estimated pivot point locations may indicate that the patient has been moved or a sensor is malfunctioning thereby giving the system an opportunity to take corrective action.

The interaction between the moving instrument and the tissue of the minimally invasive aperture may be determined at least in part by the processor, the processor optionally allowing the compliance or stiffness of the system to be changed throughout a range extending from a passive pivot point to a fixed pivot point. At the passive end of the passive/rigid range, the proximal end of the instrument may be moved in space while the motors of the instrument holder wrist joint apply little or no torque, so that the instrument acts effectively like it is coupled to the manipulator or robotic arm by a pair of passive joints. In this mode, the interaction between the instrument shaft and the tissue along the minimally invasive aperture induces the pivotal motion of the instrument about the pivot point. If the surgical instrument was not inserted into the minimally invasive aperture or otherwise constrained, it may point downward under the influence of gravity, and movement of the manipulator arm would translate the hanging instrument without pivotal motion about a site along the instrument shaft. Toward the rigid end of the passive/rigid range, the location of the minimally invasive aperture may be input or calculated as a fixed point in space. The motors associated with each joint of the kinematic chain disposed proximal of the pivot point may then drive the manipulator so that any lateral force laterally against the shaft at the calculate pivot point results in a reaction force to keep the shaft through the pivot point. Such a system may, in some ways, behave similar to mechanically constrained remote center linkages. Many embodiments will fall between these two extremes, providing calculated motion which generally pivots at the access site, and which adapts or moves the pivotal center of motion within an acceptable range when the tissue along the minimally invasive access site moves, without imposing excessive lateral forces on that tissue.

Figure 21:
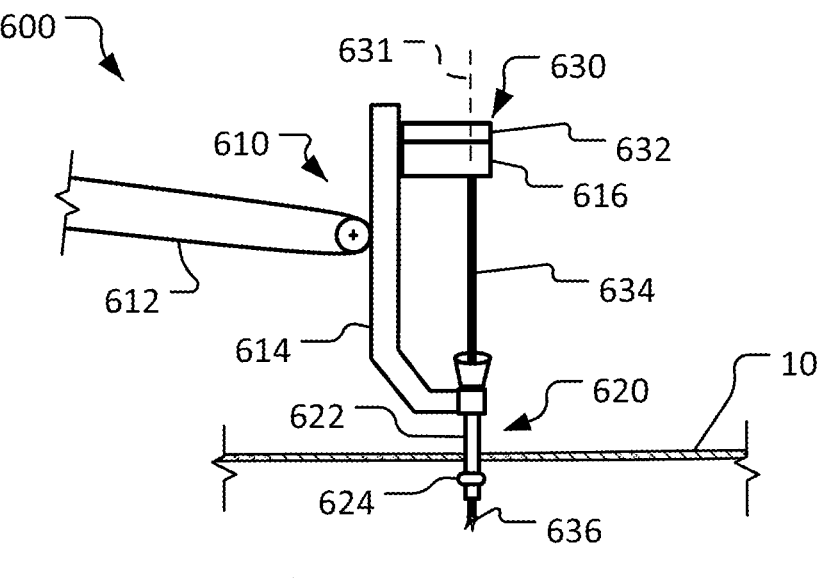
FIG. 21 is a side view of a distal portion of an example patient-side robotic manipulator arm assembly, cannula, and surgical instrument that is inserted through a body wall at a minimally invasive surgical access site.
Figure 22:
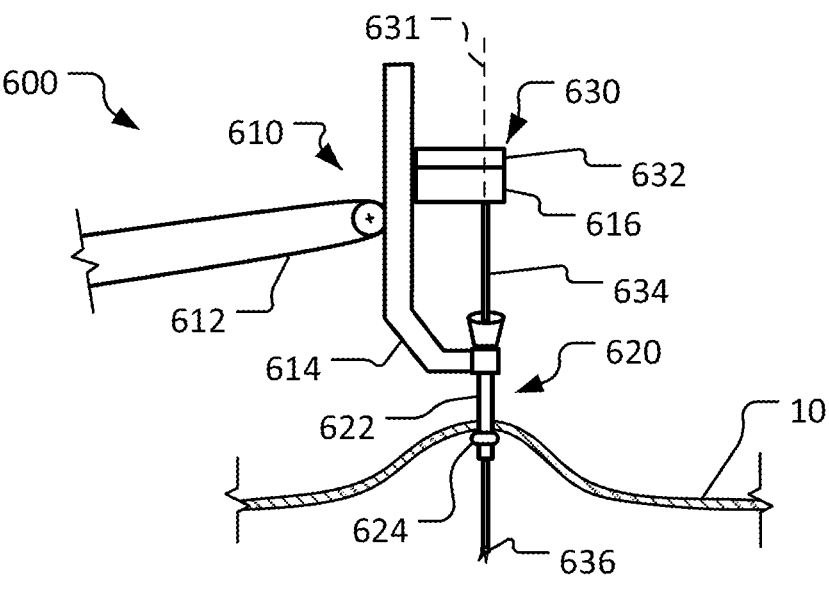
FIG. 22 is another view of the arrangement of FIG. 21 with the cannula creating a tent of the body wall to increase the internal surgical working space.

Referring to FIGS. 21 and 22, a computer-assisted surgery system 600 (or "surgery system 600") can be used to perform a minimally invasive robotic surgical method. The surgery system 600 is a portion of a computer-assisted surgery system (like a portion of the patient-side cart 100 of FIG. 1, for example). In this example, the surgery system 600 is used to tent an outer tissue layer 10 (e.g., a body wall 10 in the cases where the outer tissue layer is a body wall), thereby creating a larger surgical working space below the outer tissue layer 10. By creating a larger working space within the patient, increased surgical access and better visibility for the minimally invasive surgery can be advantageously attained. FIG. 21 shows the surgery system 600 prior to tenting the outer tissue layer 10. FIG. 22 shows the surgery system 600 after tenting the outer tissue layer 10. In some implementations, the outer tissue layer 10 is the outer body wall (outer skin, muscle, fat, etc.) of a patient through which an incision is made to access the target operative area.

The surgery system 600 includes a robotic manipulator arm assembly 610 (or "manipulator assembly 610"), a cannula 620, a surgical instrument 630, and one or more processors (not shown). The robotic manipulator arm assembly 610 includes a robotic manipulator arm 612 and an instrument holder 614. The instrument holder 614 is pivotably coupled to the robotic manipulator arm 612. The cannula 620 is releasably coupled to the instrument holder 614. The surgical instrument 630 is releasably coupled to an instrument holder carriage 616 that is controllably translatable along the instrument holder 614. In some embodiments, the processor of the surgery system 600 is configured to detect a releasable coupling of the cannula 620 to the manipulator assembly 610. In some embodiments, the processor of the surgery system 600 is configured to detect an installation of the surgical instrument 630 to the manipulator assembly 610.

The surgical instrument 630 includes a transmission assembly 632 that is releasably couplable with the instrument holder carriage 616. The surgical instrument 630 includes an elongate shaft 634 that extends from the transmission assembly 632. At the distal end of the elongate shaft 634 is an end effector 636. A variety of alternative robotic surgical instruments 630 of different types and differing end effectors 636 may be used, with the instruments sometimes being removed and replaced during a surgical procedure.

The cannula 620 defines a lumen in which the elongate shaft 634 is slidably coupled. As the instrument holder carriage 616 is translated along the instrument holder 614, the instrument 630 moves along with the instrument holder carriage 616. Consequently, the elongate shaft 634 slides within the lumen of the cannula 620. Hence, the elongate shaft 634 (and the end effector 636) becomes extended distally and/or retracted proximally in relation to the cannula 620 by translational movements of the instrument holder carriage 616 along the instrument holder 614. In such a fashion, the end effector 636 can be moved, using the processor of the surgery system 600, distally deeper into the operative space, or moved proximally away from the operative space. However, such a translation of the instrument holder carriage 616, and the instrument 630, does not involve any movement of the cannula 620.

The elongate shaft 634 defines a longitudinal axis 631 which is coincident with an axis defined by the cannula 620 and with an axis defined by the lumen of the cannula 620. As the instrument holder carriage 616 is translated along the instrument holder 614 (using the processor of the surgery system 600), the instrument 630 is moved along the longitudinal axis 631.

The cannula 620 includes a cannula shaft 622 and a tissue engagement element 624 that configures the cannula 620 to be selectively couplable with a tissue layer of a patient. In the depicted embodiment, the tissue engagement element 624 is an inflatable member that is coupled to the cannula shaft 622. FIGS. 33-36 describe various other embodiments of tissue engagement elements 624 that can be used alternatively to the depicted inflatable member. Because the depicted tissue engagement element 624 is inflatable, the tissue engagement element 624 has a deflated, low-profile configuration and an inflated, deployed configuration in which the cannula 620 is couplable with a tissue layer of a patient. The low-profile configuration of the tissue engagement element 624 can be used, for example, while inserting or removing the cannula 620 from the patient. In some embodiments, the engagement element 624 could be inflatable on both of sides of a tissue layer, allowing purchase on tissue during cannula motion in a direction into or out of the patient.

In use, the cannula shaft 622 is inserted through an incision in the outer tissue layer 10 such that the tissue engagement element 624 is positioned below the outer tissue layer 10 (i.e., within the patient). After passing the tissue engagement element 624 generally through the outer tissue layer 10, the tissue engagement element 624 can be coupled with the outer tissue layer 10. For example, in the depicted embodiment the tissue engagement element 624 can be inflated in preparation for tenting the outer tissue layer 10. Then, to tent the outer tissue layer 10, the tissue engagement element 624 is moved away from the patient (as depicted by FIG. 22 in comparison to FIG. 21).

To tent the outer tissue layer 10 as depicted in FIG. 22, the cannula 620 (with the tissue engagement element 624 coupled with the outer tissue layer 10) is moved, using the processor of the surgery system 600, away from the patient. Accordingly, in some embodiments the processor of the surgery system 600 is configured to move the cannula 620 relative to patient anatomy such that the surgical working space is modified (change in size, shape, location, etc.). In some embodiments, the processor of the surgery system 600 is configured to move the cannula 620 relative to the patient anatomy such that the surgical working space is modified by detecting a coupling of the cannula 620 to the manipulator assembly 610 (the cannula 620 being configured to couple with a tissue layer of a patient) and moving the manipulator assembly 610 such that the cannula 620 causes the tissue layer to tent and modify the surgical working space.

In some embodiments, such as the depicted embodiment, the tissue engagement element 624 is moved away from the patient along a fixed line in space that is coincident with the longitudinal axis 631. To accomplish such a movement, the software-constrained remote center of motion concepts for constraining the motion of the robotic manipulator arm assembly 610 (as described herein) can be utilized. Moving the robotic manipulator arm assembly 610, using the software-constrained remote center of motion concepts, to tent the outer tissue layer 10 minimizes lateral motion of the cannula 620 which might otherwise inadvertently stress or even tear the tissues at the incision. In some embodiments, using the software-constrained remote center of motion concepts, the robotic manipulator arm assembly 610, as controlled by the processor of the surgery system 600, can move the cannula 620 along a fixed line in space that is coincident with the longitudinal axis 631. Some or all of such constraint on the motion of the robotic manipulator arm assembly 610 may be imposed using, in part or in full, the robotic data processing and control techniques described herein.

The above example, and many of the other examples described herein, uses tenting and enlarging the working space to illustrate modification of the work space. These techniques of controlling the system interaction with tissue can be also used to move the cannula relative to the patient anatomy such that the working space is changed in size (reduced in size or enlarged), or is changed in shape, or is changed in both size and shape. For example, the cannula may be pitched or yawed, rotated, moved laterally, translated towards the working space instead of away from the working space, or any combination of cannula translation and rotation. The interaction of the cannula with the tissue layer(s) results in tissue deformation and modification of the working space.

In some embodiments, the software-constrained remote center of motion data processing and control techniques described herein can be used by the processor of the surgery system 600 to position and/or to reposition, the remote center of motion of the surgery system 600 at locations such as on the cannula 620 just proximal to the tissue engagement element 624, for example. In some such embodiments, the position of the remote center of motion may be maintained, by the processor of the surgery system 600, just proximal to the tissue engagement element 624 during the entire robotic surgical procedure. For example, the position of the remote center of motion may be just proximal to the tissue engagement element 624 in both of the arrangements depicted in FIGS. 21 and 22. Alternatively, as described further below, in some embodiments the position of the remote center of motion may be selectively adjusted or repositioned relative to the cannula 620, using the processor of the surgery system 600, during the robotic surgical procedure. Accordingly, the processor of the surgery system 600 may be configured to reposition the remote center of motion to other locations relative to the cannula 620 in response to receiving an indication to reposition the remote center of motion.

In some such embodiments, the processor is configured to reposition the remote center of motion to the second location while constraining the second location to along the cannula 620. The second location can be constrained to along the cannula 620 in a variety of ways. For example, in some such embodiments, the processor is configured to reposition the remote center of motion to the second location while constraining the second location to coincide with an axis defined by an inner surface of the shaft 622 of the cannula 620, an outer surface of the shaft 622 or the cannula 620, or a lumen of the cannula 620. As another example, in some such embodiments, the processor is configured to constrain the second location to be coincident with a central axis of part or all of the shaft 622 of the cannula 620. As another example, in some embodiments, the processor is configured to constrain the second location to being on an inner or outer surface of the cannula 620. As yet another example, in some embodiments, the processor is configured to reposition the remote center of motion to the second location while constraining the second location to within a volume surrounded by the wall of the cannula 620.

In some such embodiments, the processor is configured to reposition the remote center of motion to the second location while constraining the second location to along the shaft 634 of the instrument 630. The second location can also be constrained to along the shaft 634 in a variety of ways. For example, in some such embodiments, the processor is configured to reposition the remote center of motion to the second location while constraining the second location to coincide with an axis defined by the shaft 634, such as a central axis defined by part or all of the shaft 634. As another example, in some embodiments, the processor is configured to constrain the second location to being on an inner or outer surface of the shaft 634. As yet another example, in some embodiments, the processor is configured to reposition the remote center of motion to the second location while constraining the second location to within a volume surrounded by the wall of the shaft 634.

In some cases, a first location of the remote center of motion is along the cannula 620 and a second location of the remote center of motion (after the remote center of motion is repositioned from the first location by the processor of the surgery system 600) is not along the cannula 620. In some such cases, the processor of the surgery system 600 may be configured to limit a motion of the cannula 620 based on the second location of the remote center of motion.

In some cases, the first location of the remote center of motion and the second location of the remote center of motion (after the remote center of motion is repositioned from the first location) are at different distances from a longitudinal axis defined by the cannula 620. In some such cases, the processor of the surgery system 600 is configured to reposition the remote center of motion to the second location while constraining the second location to within a maximum distance from the longitudinal axis defined by the cannula 620.

In some embodiments, the processor of the surgery system 600 is configured to receive a command to move the instrument 630 in accordance with a commanded instrument motion, and command the instrument 630 to move with a modified instrument motion. In some such embodiments, the modified instrument motion is based on the commanded instrument motion and the second location of the remote center of motion. For example, for an end effector attached to a rigid, straight shaft, the shaft needs to pivot more about a remote center of motion located along the shaft and closer to the end effector than a remote center of motion located along the shaft and farther from the end effector. Similar considerations apply for other instrument designs with non-rigid or non-straight shafts. In some embodiments, when the motion of the instrument 630 or of the manipulator holding the instrument 630 that is needed to provide a commanded motion exceeds an acceptable limit, the instrument motion is modified so that the manipulator or instrument motion(s) are acceptable. For example, the motion of the remainder of the instrument or the manipulator holding the instrument may be scaled downwards by a constant, be scaled downwards by a variable based on the location of the remote center of motion, be capped at zero or a non-zero value, etc. As specific examples, in some embodiments, when the remote center of motion is within a threshold distance of the end effector, the processor of the surgery system 600 disallow instrument pitch, yaw, and/or roll. As further examples, when the remote center of motion is within a threshold distance of the end effector, the processor of the surgery system 600 allows only instrument wrist pitch, yaw, and/or insertion/withdraw. Limits used in modifying the instrument motion can be based on parameters to reduce or avoid damage to internal tissue, placing high tearing forces, on the body wall or inner tissue layers, etc. In some embodiments, the modifications may increase the motion of one or more links or joints of the instrument 630 or the manipulator holding the instrument 630, such as to allow a smaller motion of other links or joints, or to increase the commanded instrument motion. Feedback to the operator or other users may be provided through any appropriate manner, including by visual or aural feedback, haptic feedback (such as force feedback that resists operator movements associated reduced or limited degrees of freedom, aids operator movement associated with magnified degrees of freedom), etc.

In accordance with the preceding description regarding the repositioning of the remote center of motion by the processor of the surgery system 600 from the first location to a second location, it can be understood that this disclosure describes a computer-assisted robotic method comprising: (i) determining, by the processor of the robotic surgery system 600, the first location of a remote center of motion of the robotic surgery system 600, (ii) receiving, by the processor of the robotic surgery system 600, an indication to reposition the remote center of motion relative to the cannula 620, and (iii) repositioning, by the processor of the robotic surgery system 600 and in response to receiving the indication, the remote center of motion to a second location relative to the cannula 620. In some embodiments of the method, the first location is along the cannula 620 and the second location is not along the cannula 620. In some such cases, the method may also include limiting a motion of the cannula 620 based on the second location of the remote center of motion.

In some embodiments of the method, the first location of the remote center of motion and the second location of the remote center of motion (after the remote center of motion is repositioned from the first location) are at different distances from a longitudinal axis defined by the cannula 620. In some such cases, the step of repositioning the remote center of motion to the second location includes constraining the second location to within a maximum distance from the longitudinal axis defined by the cannula 620.

In some embodiments of the method, the method of repositioning the remote center of motion to the second location includes constraining the second location to along the cannula 620. In some embodiments of the method, the method of repositioning the remote center of motion to the second location includes constraining the second location to coincide with an axis defined by a lumen of the cannula 620. In some embodiments of the method, the method of repositioning the remote center of motion to the second location includes constraining the second location to along the shaft 634 of the instrument 630. In some embodiments of the method, the method of repositioning the remote center of motion to the second location includes outputting, by the processor, one or more signals to cause the manipulator assembly 610 to move the cannula 620 and the instrument 630 relative to each other such that the first location of the remote center of motion and the second location of the remote center of motion are at a same location relative to the instrument 630.

In some embodiments of the method, the method of repositioning the remote center of motion to the second location includes receiving a command to move the instrument 630 in accordance with a commanded instrument motion, and commanding the instrument 630 to move with a modified instrument motion. In some such embodiments, the modified instrument motion is based on the commanded instrument motion and the second location of the remote center of motion. In some embodiments of the method, the method of repositioning the remote center of motion to the second location includes outputting, by the processor, one or more signals to cause the manipulator assembly to move the instrument 630 while holding the cannula 620 stationary.

In some embodiments of the method, the method of repositioning the remote center of motion to the second location includes limiting a speed of motion of the remote center of motion. In some embodiments of the method, the method of repositioning the remote center of motion to the second location includes determining a force associated with the cannula 620, and disallowing motion of the remote center of motion in response to the force associated with the cannula 620 exceeding a force limit. The force(s) associated with the cannula 620 may be determined through models, measurements, or a combination of models and measurements. For example, forces on the cannula 620 may be calculated by using an estimate of the deflection of the tissue contacting the cannula 620 and average or previously measured physical properties of the anatomy (e.g. geometry, admittance, etc.) As another example, forces on the cannula 620 may be measured by force sensors located on the cannula. As yet another example, forces on the cannula 620 may be estimated by measuring the deflections of one or more joints of a structure holding the cannula 620 (such as a robotic manipulator) and using a mechanical model of the structure to derive the forces associated with a deflection. In some embodiments of the method, the method of repositioning the remote center of motion to the second location includes providing a visual indication of the remote center of motion.

Tenting of the outer tissue layer 10, as depicted in FIG. 22, may be particularly advantageous for robotic surgeries in locations of the body that have shallow surgical working spaces. Said differently, tenting of the outer tissue layer 10 may be particularly advantageous for robotic surgeries in locations of the body where the entry point through the outer tissue layer 10 is close to the operative point/area.

Figure 23:
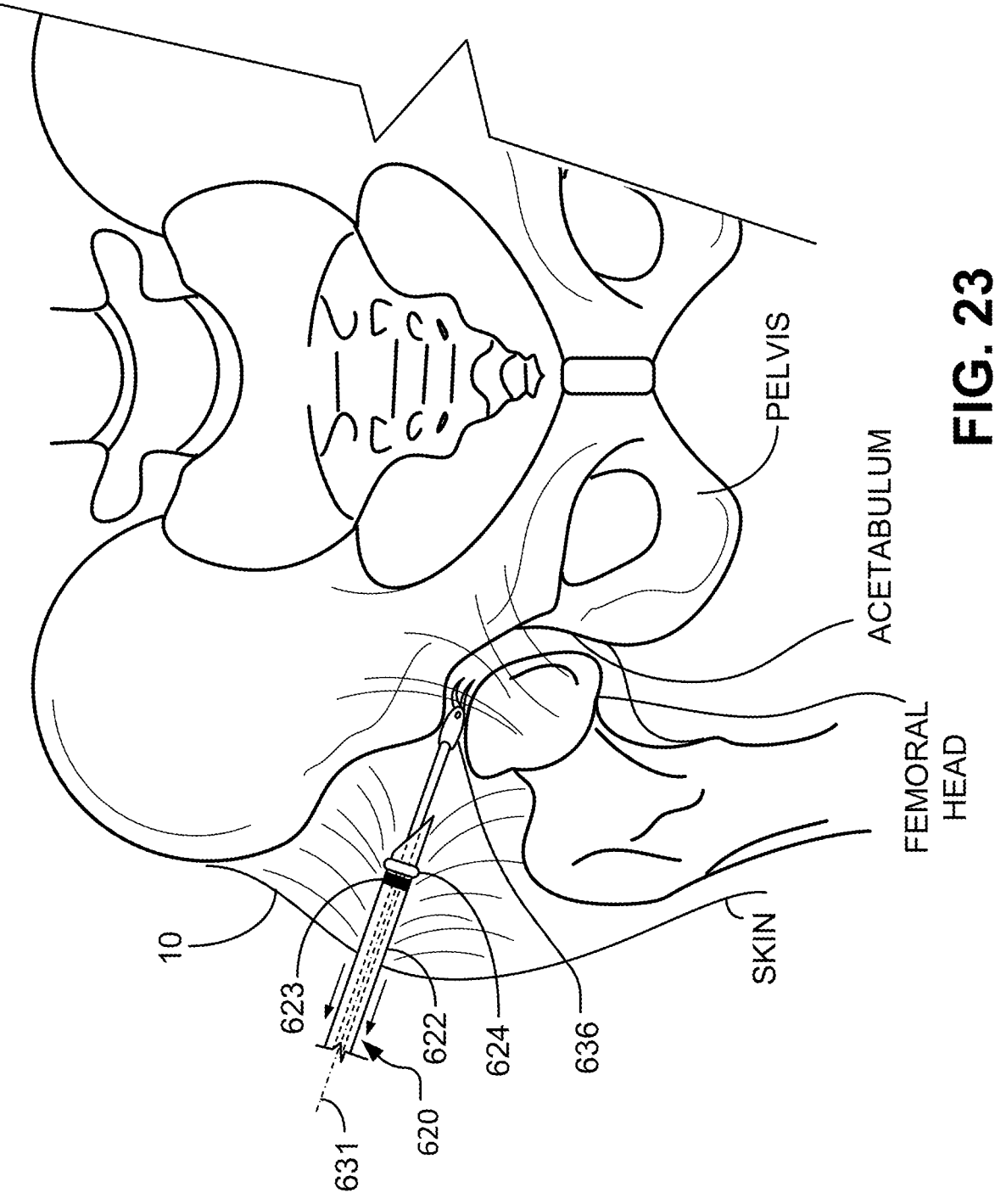
FIG. 23 depicts an example surgical scenario for which the tenting of the body wall using the techniques of FIG. 22 is particularly advantageous.

One non-limiting example of a robotic surgery technique that has an entry point through the outer tissue layer 10 that is close to the operative point/area is shown in FIG. 23. Here, a hip surgery is depicted as being performed using the devices, systems, and methods provided herein. That is, the tissue engagement element 624 attached to the cannula shaft 622 is being pulled outward from the patient to create a larger surgical working space within the patient near the ball and socket joint of the hip. In some embodiments, the software-constrained remote center of motion concepts as described herein are used to move the cannula 620 along a fixed line in space that is coincident with the longitudinal axis 631 to tent the tissue layer 10.

In the depicted embodiment, the manipulator assembly's remote center of motion is coincident with a position 623 on the cannula shaft 622. As such, the position 623 may be referred to herein as "position 623," "remote center of motion position 623," or "remote center of motion 623." As depicted, in some embodiments the position 623 of the remote center of motion can be proximally adjacent to the tissue engagement element 624. During and after the depicted movement of the cannula 620 along the fixed line in space that is coincident with the longitudinal axis 631, in some embodiments the position 623 of the manipulator arm assembly's remote center of motion remains in a fixed location relative to the cannula 620. The software-constrained remote center of motion concepts described herein can be used to control the robotic manipulator arm assembly 610 to move the cannula 620 along the fixed line in space that is coincident with the longitudinal axis 631, and to maintain the remote center of motion at position 623.

While in the example scenario of FIG. 23, the robotic manipulator arm assembly 610 is controlled, by the processor of the surgery system 600, to maintain the remote center of motion at fixed position 623 on the cannula while the cannula 620 is moved, in some robotic surgical methods the position of the remote center of motion is advantageously not maintained in a fixed position 623 on the cannula 620, but is rather repositioned to a second location relative to the cannula 620 that is different from a first location relative to the cannula 620. Moreover, in some embodiments the processor of the surgery system 600 is configured to reposition the remote center of motion from such a first location to such a second location while the processor is programmed and controlled to be constrained in any one or more of the following manners. The processor may be constrained to keep the second location to within a maximum distance from a longitudinal axis of the cannula 620. The processor may be constrained to keep the second location along the cannula 620. The processor may be constrained to keep the second location coincident with an axis defined by a lumen of the cannula 620. The processor may be constrained to keep the second location along the shaft 634 of the instrument 630. The processor may be constrained to limit a speed of motion of the remote center of motion. The processor may be constrained from further repositioning of the remote center of motion in response to reaching or exceeding a force limit detected by the cannula 620 (using one or more strain gauges on the cannula 620, for example). The processor may be constrained from actuating motions of one or more particular degrees of freedom based on the repositioning of the remote center of motion. In some embodiments the processor of the surgery system 600 is configured to reposition the remote center of motion from a first location on the cannula 620 to a second location that is not along the cannula 620.

FIGS. 24-26 provide an example computer-assisted tele-operated surgery method in which the remote center of motion position 623 is not maintained at a fixed position on the cannula 620 during the robotic surgical procedure. In this example method, the remote center of motion position 623 can be maintained, for example, by the processor of the surgery system 600 at a fixed position on the elongate shaft 634 of the instrument 630. In some embodiments, the processor can be configured to output the one or more signals to cause the manipulator assembly 610 to move the cannula 620 and the instrument 630 relative to each other by outputting, by the processor, one or more signals to cause the manipulator assembly 610 to move the instrument 630 while holding the cannula 620 stationary. As the shaft 634 of the instrument 630 is moved, the remote center of motion position 623 is repositioned, by the processor of the surgery system 600, correspondingly such that a first location of the remote center of motion and a second location of the remote center of motion are at a same location relative to the instrument 630. Alternatively, the remote center of motion position 623 can be selectively located and/or repositioned, using the processor of the surgery system 600, at various positions along the elongate shaft 634 of the instrument 630, or even at locations off the shaft 634.

In the computer-assisted tele-operated surgery method depicted in FIGS. 24-26, the surgery system 600 is used to perform a minimally invasive robotic surgical method within an elongate surgical working space 14. In FIG. 24, the end effector 636 is at a first location. In FIG. 25, the end effector 636 is at a second location that is deeper within the elongate surgical working space 14 than the first location. In FIG. 26, the end effector 636 is at a third location that is deeper within the elongate surgical working space 14 than the second location.

In this example scenario, the elongate surgical working space 14 is curved. In some scenarios, the elongate surgical working space 14 has more than one curve, or is irregularly shaped, in three-dimensional space. In some scenarios, the elongate surgical working space 14 is generally straight. The use of the methods described here can assist with successful navigation of the surgical instrument 630 along all such elongate surgical working spaces 14.

In each of the depicted arrangements, the remote center of motion position 623 is maintained, by the processor of the surgery system 600, at a fixed position on the elongate shaft 634 of the instrument 630. That is, the remote center of motion position 623 is at the same position on the elongate shaft 634 of the instrument 630 in each of the arrangements shown in FIGS. 24-26. It can be envisioned that the remote center of motion position 623 followed a curved path as it transitioned between the arrangements shown in FIGS. 24-26. Such a curved path can be important to avoid interference with the walls of the elongate surgical working space 14.

It should be understood that remote center of motion position 623 can be selectively positioned, by the processor of the surgery system 600, anywhere along the shaft 634, or even at locations off the shaft 634. In some embodiments, the software-constrained remote center of motion data processing and control techniques described herein can be used such that the processor can position the remote center of motion of the surgery system 600 in the location(s) as desired. The particular shape and depth of the elongate surgical working space 14 may make some remote center of motion positions 623 more advantageous than others. Hence, in some cases the surgeon operating the surgery system 600 may select a particular method for processor control of the remote center of motion position 623 in accordance with the particular surgical scenario being presented. Such methods may include, but are not limited to, keeping or constraining the remote center of motion position at a constant location on the cannula 620, at a constant location on the instrument shaft 634, at a constant location in space, at locations along the axes of the cannula 620 and instrument shaft 634, at locations along the axes of the cannula 620 and instrument shaft 634, and the like, and combinations thereof. Alternatively, in some cases the surgeon operating the surgery system 600 may manually control/adjust, using the processor of the surgery system 600, the remote center of motion position 623, and/or the method of controlling the remote center of motion position 623, one or more times during the surgical procedure.

Figures 27, 28:
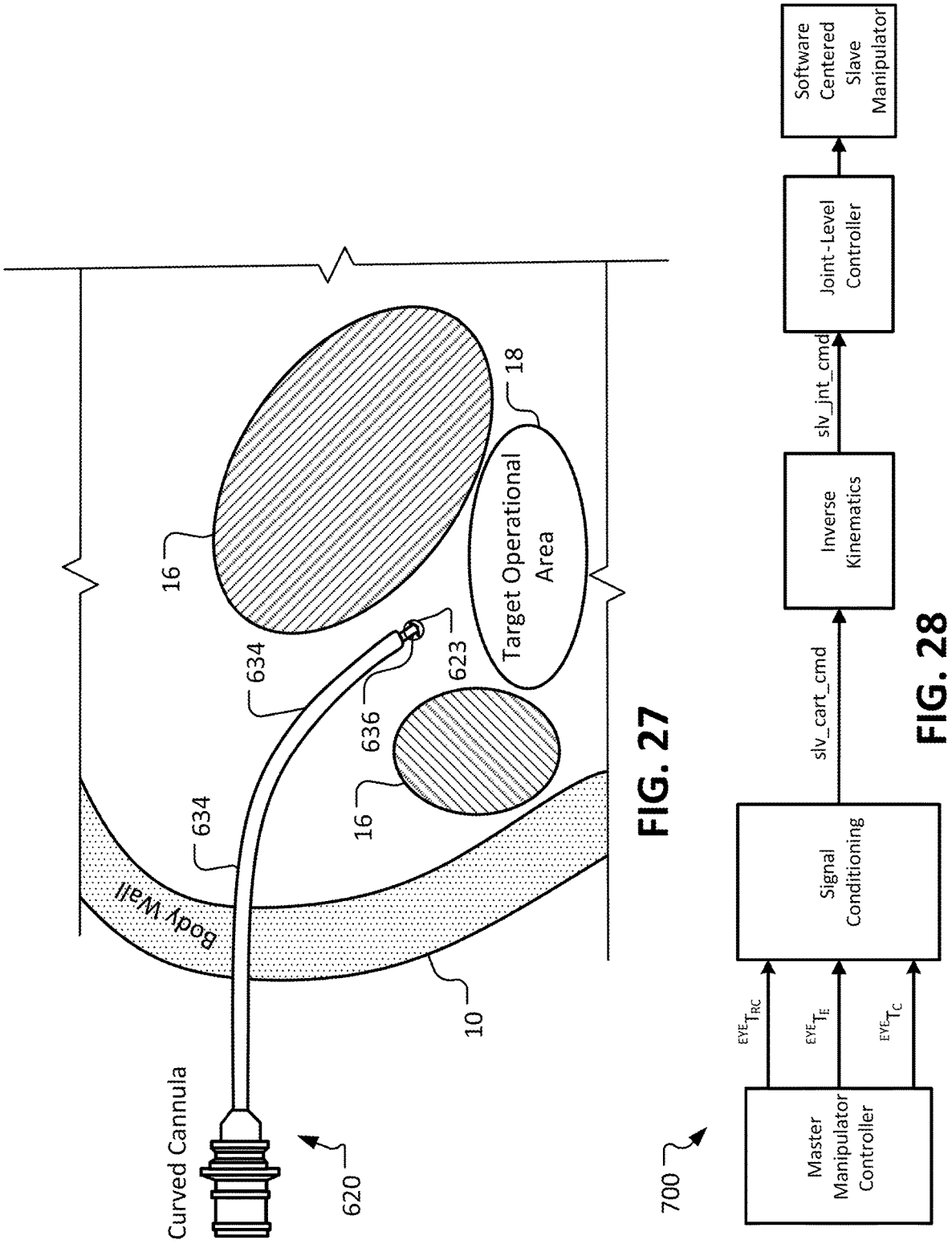
FIG. 27 depicts an example surgical scenario for which the techniques described in reference to FIGS. 24-26 are particularly advantageous.
FIGS. 28-30 are example schematic block diagrams for frame of reference motion control in accordance with some embodiments.

FIG. 27 provides another non-limiting example surgical scenario for which the method of controlling the remote center of motion position 623 at a fixed position on the elongate shaft 634 of the instrument 630 can be advantageous. In this scenario, there are one or more sensitive areas 16 within the patient near the target operational area 18. The instrument shaft 634 must be navigated such that the end effector 636 accesses the target operational area 18, but the sensitive areas 16 must be avoided. That is, the sensitive areas 16 must not be contacted by the instrument shaft 634 during the procedure. In such a case, it can be advantageous to locate, using the processor of the surgery system 600, the remote center of motion position 623 at a location near to the end effector 636, or at a short distance proximal thereto.

Figure 29:
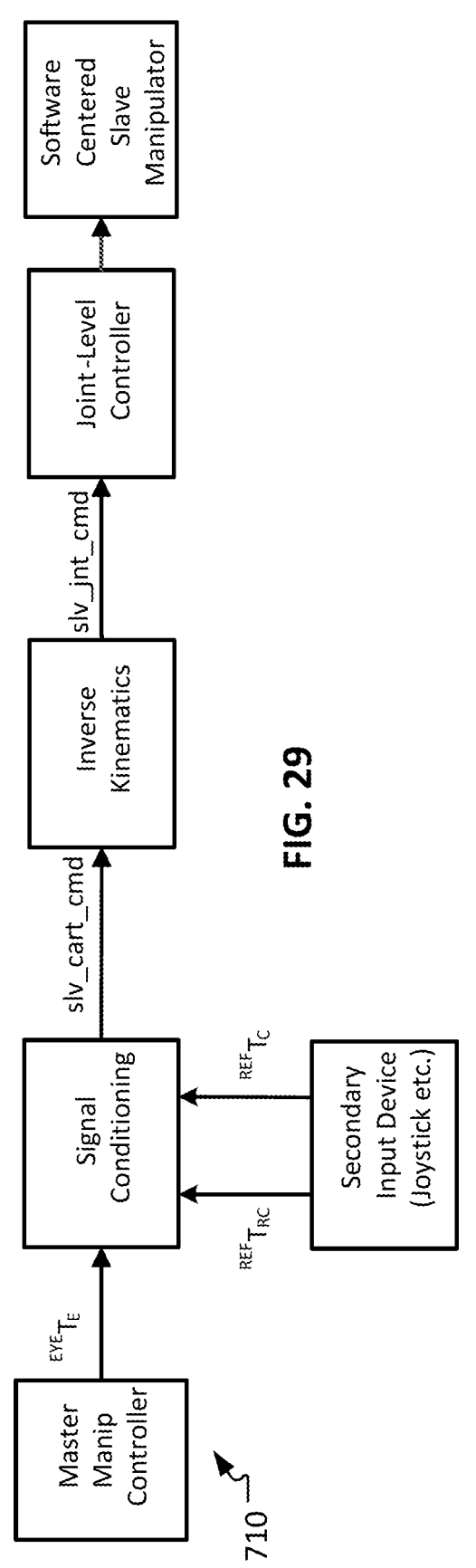
Figure 30:
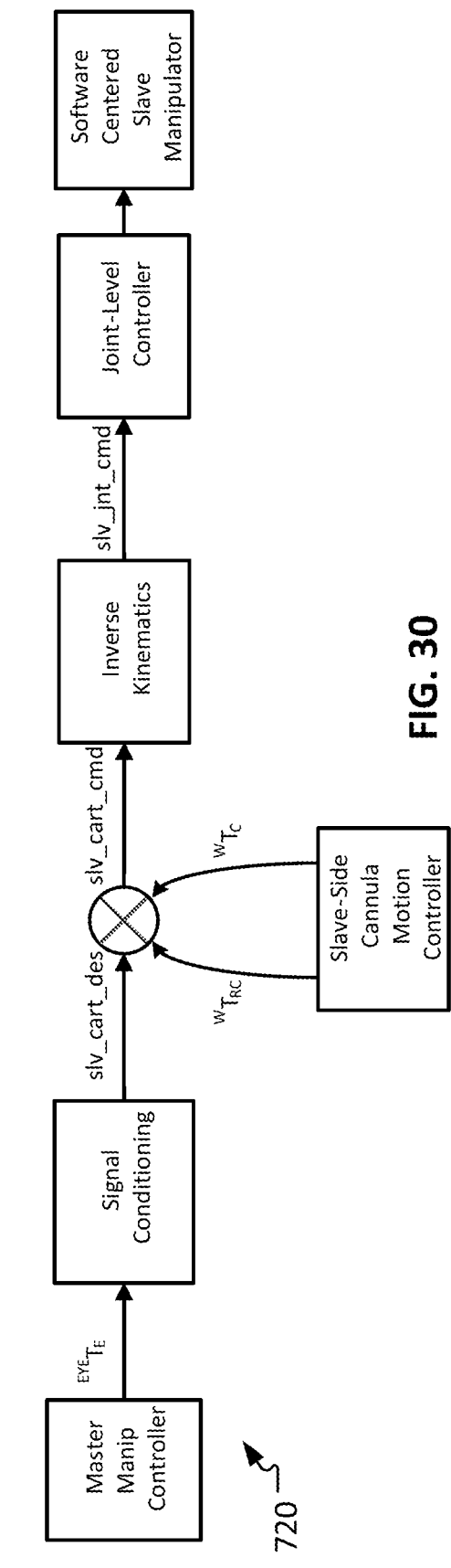

Referring to FIGS. 28-30, there are at least three frames of reference to be controlled by the system's controller (e.g., processor 43 of FIG. 2). One of the frames of reference (C) is that of the cannula 620 (the others include the remote center of motion position 623 frame of reference, RC, and the instrument end-effector 636 frame of reference, E). Generic block diagrams for frame of reference motion control may be represented as shown in FIGS. 28-30. These figures show options for commanding the cannula, instrument, and remote center frame of reference motions in relation to a relevant reference (depending on the input modality).

Assume that $^{EYE}T_E$ is commanded by the master tool manipulator (MTM) controller (e.g., processor 43 of FIG. 2). The pose specification for the remote center and cannula frames of reference could come from one or a combination of the following sources: (i) MTM controller specifying these frames in the EYE frame, i.e. $^{EYE}T_{RC}$ and $^{EYE}T_C$, (ii) a secondary device commanding these frame poses in a convenient reference frame, i.e. $^{REF}T_{RC}$ and $^{REF}T_C$ (where $^{EYE}T_{REF}$ can be determined), and (iii) a slave-side controller specifying these poses in the slave arm's base frame, i.e. $^{W}T_{RC}$ and $^{W}T_C$ (where $^{EYE}T_W$ is known). Specific non-limiting embodiments of these are shown in FIGS. 28-30.

FIG. 28 is a block diagram 700 for actively controlling the remote center of motion (RC), cannula (C), and instrument end-effector (E) frames of reference using inputs from the MTM controller. This control modality may be relevant to an embodiment such as, but not limited to, the "trombone" and other relative MTM movement control modes (described further below in reference to FIG. 40). Although FIG. 40 describes this control technique largely in conjunction with tenting the body wall, similar control methodology can be used for moving the remote center of motion regardless of any effect on the body wall or any associated working space.

In accordance with these descriptions, it can be envisioned that this disclosure describes a system comprising an operator console comprising one or more handheld input devices, where the operator console provides the indication to reposition the remote center of motion in response to a signal from the handheld input device. The signal from the handheld input device may be triggered by actuation of buttons, switches, or other sensors on the input device, or by motion of the input device.

Further, it can be envisioned that this disclosure describes a system comprising first and second handheld input devices in electrical communication with the processor, where the indication to reposition the remote center of motion comprises a signal indicating relative motion of the first handheld input device away from the second handheld input device. The first and second handheld input devices may be attached to a console or be free floating. The relative motion of the first handheld input device may be due to motion of the first handheld input device, motion of the second handheld input device, or motion of both the first and second handheld input devices.

FIG. 29 is a block diagram 710 for actively controlling instrument end-effector (E) frame using inputs from the master manipulator controller, while controlling the remote center (RC) and cannula (C) frames using a secondary input device. Note that the secondary input device may use an arbitrary reference for convenience and not necessarily the eye frame. However, the reference frame transformation $^{EYE}T_{REF}$ can be directly measured or computed from indirect measurements. The signal conditioning unit may then combine these inputs in an appropriate common frame for use by the slave manipulator controller.

FIG. 30 is a block diagram 720 for actively controlling instrument end-effector (E) frame using inputs from the master manipulator controller, while controlling the remote center (RC) and cannula (C) frames using a slave side interface. Note that the slave side inputs may be provided in an arbitrary reference frame such as the world frame used for control by the slave manipulator controller. A 6-DOF transformation between the robot's world frame and to the eye fixed frame (EYE) may be directly measured or computed from indirect measurements. This block diagram may be used in an embodiment where independent cannula motion is commanded at the slave side by the three-state switch or in a clutch mode as described further below.

Figure 31:
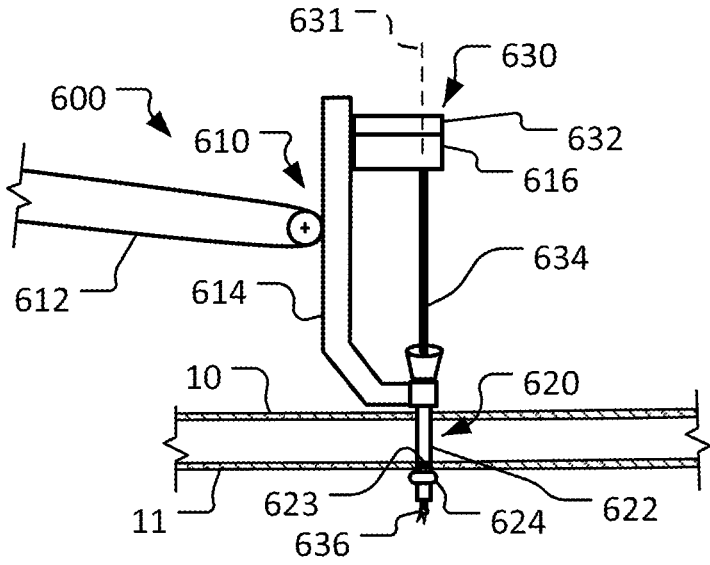
FIG. 31 is a side view of a distal portion of an example patient-side robotic manipulator arm assembly, cannula, and surgical instrument that is inserted through an outer body wall and an inner tissue layer at a minimally invasive surgical access site.
Figure 32:
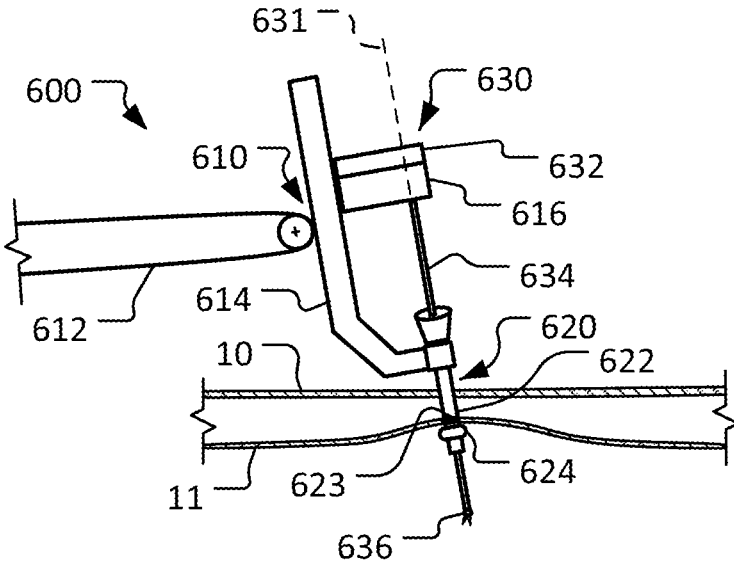
FIG. 32 is another view of the arrangement of FIG. 31 with the cannula creating a tent of the inner tissue layer to increase the internal surgical working space.

Referring to FIGS. 31 and 32, the surgery system 600 can be used to perform another minimally invasive robotic surgical method. In this example method, the surgery system 600 is used to tent an inner tissue layer 11 (e.g., a wall of an internal organ), thereby creating a larger surgical working space below the inner tissue layer 11. In a variation of this method, one or more inflatable tissue engagement elements 624 can be used on both sides of the inner tissue layer 11 to manipulate it. By creating a larger working space within the patient, increased surgical access and better visibility for the minimally invasive surgery can be advantageously attained. FIG. 31 shows the surgery system 600 prior to tenting the inner tissue layer 11. FIG. 32 shows the surgery system 600 after tenting the inner tissue layer 11. In some implementations, the inner tissue layer 11 is the wall of an organ or other cavity (e.g., colon) through which an incision is made to access the target operative area within the organ.

In use, the cannula shaft 622 is inserted through incisions in the outer tissue layer 10 (e.g., body wall) and the inner tissue layer 11 such that the tissue engagement element 624 is positioned below the inner tissue layer 11 (i.e., within the patient). After passing the tissue engagement element 624 generally through the inner tissue layer 11, the tissue engagement element 624 can be coupled with the inner tissue layer 11. For example, in the depicted embodiment the tissue engagement element 624 can be inflated in preparation for tenting the inner tissue layer 11. Then, to tent the inner tissue layer 11, the tissue engagement element 624 is moved away from the patient (as depicted by FIG. 32 in comparison to FIG. 31).

To tent the inner tissue layer 11 as depicted in FIG. 32, the cannula 620 (with the tissue engagement element 624 coupled with the inner tissue layer 11) is moved away from the patient. In some embodiments, the tissue engagement element 624 is moved away from the patient along a fixed line in space that is coincident with the longitudinal axis 631. To accomplish such a movement, the software-constrained remote center of motion concepts for constraining the motion of the robotic manipulator arm assembly 610 (as described herein) can be utilized. Moving the robotic manipulator arm assembly 610 using the software-constrained remote center of motion concepts to tent the inner tissue layer 11 minimizes lateral motion of the cannula 620 which might otherwise inadvertently stress or even tear the tissues at the incisions. In some embodiments, using the software-constrained remote center of motion concepts, the robotic manipulator arm assembly 610 can move the cannula 620 along a fixed line in space that is coincident with the longitudinal axis 631. Some or all of such constraint on the motion of the robotic manipulator arm assembly 610 may be imposed using, in part or in full, the robotic data processing and control techniques performed and/or executed by the processor of the surgery system 600 as described herein.

In some embodiments, the software-constrained remote center of motion data processing and control techniques performed and/or executed by the processor of the surgery system 600 as described herein can be used to position the remote center of motion position 623 of the surgery system 600 on the cannula 620 just proximal to the tissue engagement element 624. In some such embodiments, the position of the remote center of motion position 623 may be maintained, by the processor of the surgery system 600, just proximal to the tissue engagement element 624 during the tenting of the inner tissue layer 11 and during the entire robotic surgical procedure. For example, the position of the remote center of motion position 623 may be just proximal to the tissue engagement element 624 in both of the arrangements depicted in FIGS. 31 and 32. Alternatively, as described further below, in some embodiments the position of the remote center of motion position 623 may be selectively adjusted, using the processor of the surgery system 600, during the robotic surgical procedure.

Locating and maintaining the position of the remote center of motion position 623 on the cannula 620 at the inner tissue layer 11 as depicted can provide advantages in some surgical scenarios. For example, such a technique may be particularly beneficial when the inner tissue layer 11 is more sensitive to lateral motion than the outer tissue layer 10. For example, in the case of minimally invasive heart surgery (when the surgical working space is internal to the heart), the incision through the heart wall may be more sensitive to lateral motion than the incision through the body wall (e.g., chest wall or abdomen wall). Using the software-constrained remote center of motion concepts performed and/or executed by the processor of the surgery system 600 as described herein, the remote center of motion position 623 can be positioned at the site of the incision through the inner tissue layer 11 to thereby minimize lateral motion of the inner tissue layer 11, while allowing some lateral motion at the incision through the outer tissue layer 10.

Referring to FIG. 33, in some embodiments a robotic manipulator arm assembly can include a vacuum tissue engagement member 740. Such a vacuum tissue engagement member 740 can selectively couple with a tissue surface to facilitate tenting of the tissue or manipulation of the layer using the methods described herein.

In the depicted arrangement, the cannula 620 is releasably coupled with the instrument holder 614. The instrument holder 614 is pivotably coupled with a robotic manipulator arm 612 (not shown; refer to FIGS. 21 and 22). The vacuum tissue engagement member 740 is also releasably coupled with the instrument holder 614.

The vacuum tissue engagement member 740 includes a vacuum line 742 and a suction member 744 (or "suction device 744") in fluid communication with the vacuum line 742. The vacuum line 742 has one or more lumens that convey a negative pressure (below ambient room pressure) to the suction member 744. The suction member 744 is configured with one or more openings that can engage with the tissue surface and that can apply suction to the tissue surface by virtue of negative pressure in the suction member 744. Hence, while suction is applied by the suction member 744 to the tissue surface, the vacuum tissue engagement member 740 is coupled with the tissue.

While the vacuum tissue engagement member 740 is coupled with the tissue, the instrument holder 614 can be moved to create a corresponding movement of the tissue. For example, the instrument holder 614 can be moved away from the tissue to tent the tissue as depicted in FIG. 22.

In the depicted embodiment, the suction member 744 surrounds the cannula shaft 622. It should be understood that other arrangements are also envisioned within the scope of this disclosure. For example, in some embodiments a single vacuum cup may be used. In some embodiments, multiple discreet vacuum cups may be used. The multiple cups may be arranged in various ways, such as around the cannula shaft 622. The suction member 744 may comprise a compliant material that can conform to irregular tissue surface topographies.

Referring to FIGS. 34-36, in some embodiments a robotic manipulator arm assembly can include a mechanical tissue engagement member 750. Such a mechanical tissue engagement member 750 can selectively couple with a tissue layer to facilitate tenting of the tissue layer using the methods described herein.

In the depicted arrangement, the cannula 620 (which is releasably coupleable with a robotic manipulator arm assembly, e.g., robotic manipulator arm assembly 610 shown in FIGS. 21 and 22) is slidably coupled with the mechanical tissue engagement member 750. That is, the mechanical tissue engagement member 750 can be slid longitudinally, and can be rotated, in relation to the cannula shaft 622. In the depicted embodiment, the cannula 620 includes a lumen 625 in which the mechanical tissue engagement member 750 is slidably coupled.

The mechanical tissue engagement member 750 includes a grasping portion 752, a shaft 754, and a hook portion 756. The shaft 754 extends between the grasping portion 752 and the hook portion 756. The grasping portion 752 can be used by a clinician to manipulate the hook portion 756. For example, after the cannula shaft 622 is inserted through an incision in a tissue layer, a clinician can manipulate the grasping portion 752 to engage the hook portion 756 with an underside of the tissue layer. In some cases, the manipulation includes a rotation of the grasping portion 752 to rotate the hook portion 756. Thereafter, the robotic manipulator arm assembly can be moved away from the patient to tent the tissue layer (e.g., as described in reference to FIG. 22 or 32). In some cases, the hook portion 756 may puncture the underside of the tissue layer. In some cases, the hook portion 756 may be configured with an atraumatic end that will prevent or inhibit a puncturing the underside of the tissue layer.

A number of different designs of tissue engagement members have been described. In addition, other devices and techniques for engaging a robotic manipulator arm assembly with a tissue layer are envisioned within the scope of this disclosure. For example, in some embodiments the cannula (or an attachment thereto) can be sutured to the tissue layer. Moreover, in some embodiments a flange can be selectively deployed from the cannula. For example, a flange constructed of flexible or super-flexible materials can be contained within a lumen of the cannula, and then deployed to extend radially outward after a distal end of the cannula has been placed through an incision of the tissue layer. The deployed flange can be used to apply a retraction force to tent the tissue by moving the robotic manipulator arm assembly away from the patient. Further, inflatable tissue engagement members have been described (FIGS. 21 and 22). In some embodiments, two or more inflatable tissue engagement members can be coupled to a single cannula. In some such embodiments, a first inflatable engagement member can be positioned below the tissue layer and a second inflatable engagement member can be positioned above the tissue layer. In some cases, the inflatable engagement members can function as seals in addition to force applications for tenting the tissue layer.

Figures 37, 38, 39:
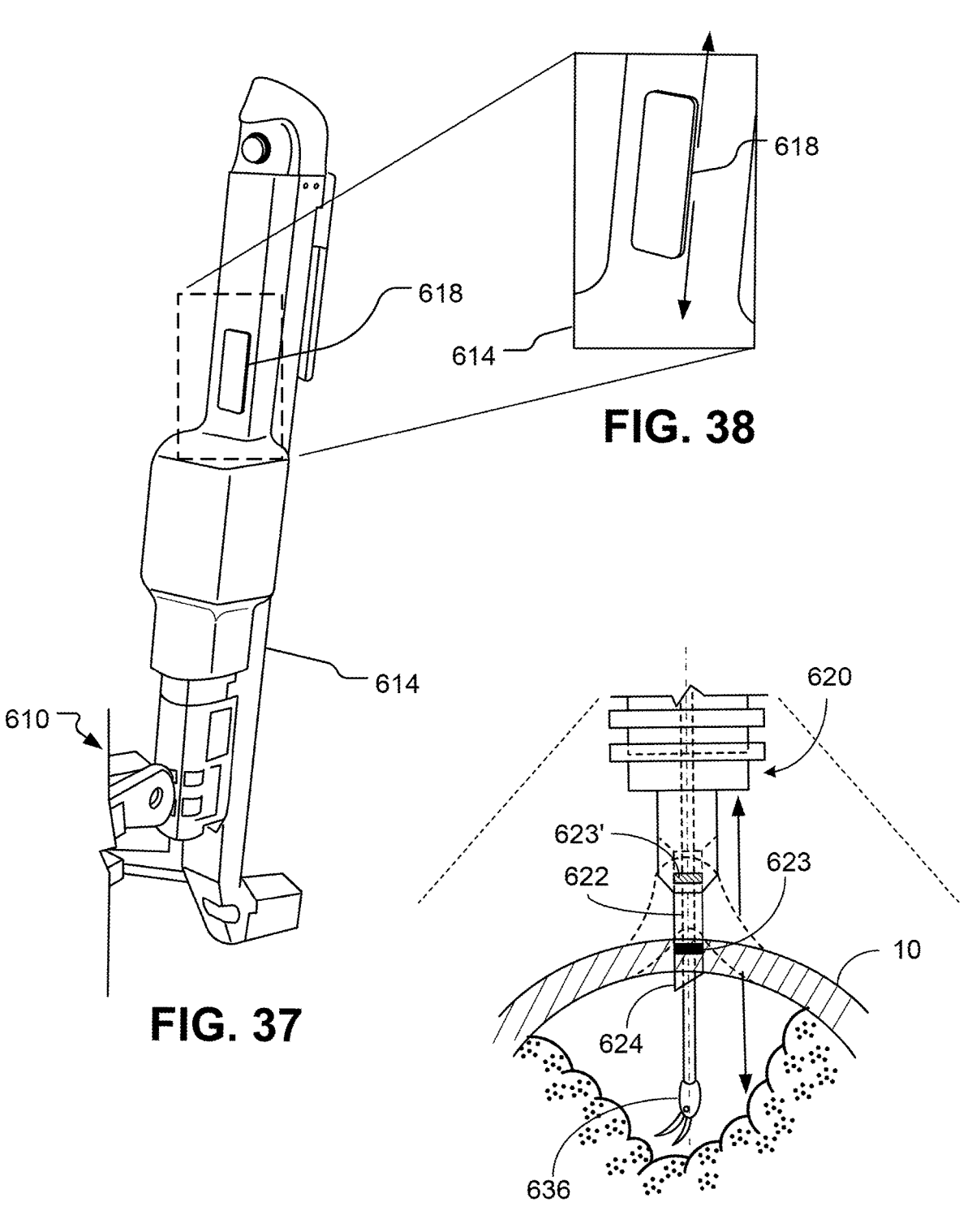
FIGS. 37 and 38 show a distal portion of an example patient-side robotic manipulator arm assembly with a switch that can be used in conjunction with some of the methods provided herein.
FIG. 39 shows a distal portion of a cannula and surgical instrument at a minimally invasive surgical site to illustrate the use of the switch of FIGS. 37 and 38.

Referring to FIGS. 37-39, in some embodiments the movements of the robotic manipulator arm assembly 610 to create a tissue tent (as described herein) can be initiated by actuating an input means such as a three-state switch 618 on the instrument holder 614 of the manipulator assembly 610. That is, a velocity control mode can be used whereby a clinician can cause the body wall 10 to tent by actuating the three-state switch 618 in a first direction, thereby sending an indication to the processor of the surgery system 600 to reposition the remote center of motion (e.g., reposition the remote center of motion relative to the cannula 620). In response to receiving the activation signal from the three-state switch 618, the robotic manipulator arm assembly 610 (and cannula 620 with a tissue engagement element 624) moves away from the patient. In some cases, the remote center of motion may also be moved relative to the cannula 620. The movement of the cannula 620 will cause the tissue engagement element 624 to exert a force on the body wall 10 such that the body wall 10 will tent. Releasing the three-state switch 618 will cause the movement of the robotic manipulator arm assembly 610 to stop and maintain the position in space. When the tissue tent is no longer desired, the clinician can activate the three-state switch 618 in a second direction that is opposite to the first direction. In response to receiving the activation signal from the three-state switch 618 in the second direction, the robotic manipulator arm assembly 610 will move toward the patient and the tent of the body wall 10 will diminish.

In the depicted arrangement and technique, the location of the remote center of motion position 623 is kept or constrained by the processor of the surgery system 600 at a consistent location on the cannula shaft 622. Therefore, as the robotic manipulator arm assembly 610 is moved away from the patient by actuation of the three-state switch 618 in the first direction, the location of the remote center of motion position 623 follows the movement of the cannula 620. In the depicted example, the location of the remote center of motion position 623 moves, by the processor of the surgery system 600, to location 623'.

Alternatively, in some embodiments the processor of the surgery system 600 may maintain the location of the remote center of motion position 623 in the same location in space despite movements of the robotic manipulator arm assembly 610 (and the cannula 620) initiated by actuation of the three-state switch 618. That is, in some embodiments activation of the switch 618 sends to the processor of the surgery system 600 the indication to reposition the remote center of motion relative to the cannula 620.

While in this example movements of the robotic manipulator arm assembly 610 to tent the body wall 10 are initiated by actuation of the three-state switch 618, other input means and techniques for moving the robotic manipulator arm assembly 610 (and/or the position of the remote center of motion) are also envisioned within the scope of this disclosure. For example, the processor of the surgery system may be configured to generate the indication to reposition the remote center of motion relative to the cannula in any appropriate manner. In various embodiments, the processor may generate the indication based on preplanned manipulator or remote center of motion trajectories, in response to detecting particular anatomical features, based on analysis of previous procedures of the same type, etc. As another example, the processor of the surgery system may be configured to receive (from external to the processor) the indication to reposition the remote center of motion relative to the cannula. The indication may be initiated by user interaction with an input means. The indication may be provided by a second processor separate from the processor. The indication may originate from a combination of the foregoing. For example, in some embodiments, the processor is configured to generate the indication in response to certain criteria or at certain parts of the procedure, and is also configured to receive the indication externally.

As further examples, in some embodiments a movement distance, i.e. the distance between 623 and 623' in the above description (e.g., a number of millimeters) can be entered into a user interface for the robotic manipulator arm assembly 610. In some embodiments, foot pedals can be used to cause the movement of the robotic manipulator arm assembly 610 (and/or the position of the remote center of motion). The foot pedals can be located, for example, at the surgeon console (e.g., surgeon console 40 of FIG. 2), or at the patient-side area. In some embodiments, voice commands and speech recognition can be used to input a distance for movement of the robotic manipulator arm assembly 610 (and/or the position of the remote center of motion) to create a tented body wall 10. Also, the surgery system may include an operator console comprising a handheld input device, where the operator console provides the indication to reposition the remote center of motion in response to a signal from the handheld input device. The surgery system may include first and second handheld input devices in electrical communication with the processor, where the indication to reposition the remote center of motion comprises a signal indicating relative motion of the first handheld input device away from the second handheld input device.

In some embodiments, a clutching mode input means can be used to tent the body wall 10 and/or to initiate repositioning of the remote center of motion. Using the clutching mode, a button on the instrument holder 614 can be depressed to allow hand movement of the instrument holder 614 away from the patient. Depression of the button releases the robotic manipulator arm assembly 610 so that it can be manually moved. After moving the instrument holder 614 to the desired location relative to the patient, the button can be released and the robotic manipulator arm assembly 610 will once again be ready for normal operations. In some software-constrained remote center embodiments, this clutching mode may be activated during surgery. In some embodiments, activation of the switch (i.e., the button on the instrument holder 614) followed by a manual movement of the manipulator assembly 610 sends to the processor of the surgery system 600 the indication to reposition the remote center of motion relative to the cannula 620.

In another example, an admittance control mode can be used to tent the body wall 10 (and/or to move the position of the remote center of motion). Using the admittance mode, a clinician can simply manually move the instrument holder 614 away from the patient to a desired location. The admittance can be tuned to match the properties of the tissue manipulated or tented. After moving the instrument holder 614 to the desired location relative to the patient, the robotic manipulator arm assembly 610 will once again be ready for normal operations. In some software-constrained remote center embodiments, this admittance control mode may be activated during surgery. In some embodiments, haptic feedback can be provided to the clinician in such admittance control mode. This type of haptic feedback may be any appropriate feedback. For example, the feedback may comprise predetermined vibration patterns or force magnitudes and directions associated with different amounts of tenting. As other examples, the feedback may be based on the admittance, may model the forces associated with manual manipulation of the cannula 620 to tent the body wall 10, may model the reaction forces experienced by the instrument holder 614 or manipulator arm assembly 610 or other structure corresponding to the tenting of the body wall 10, or the like.

Figure 40:
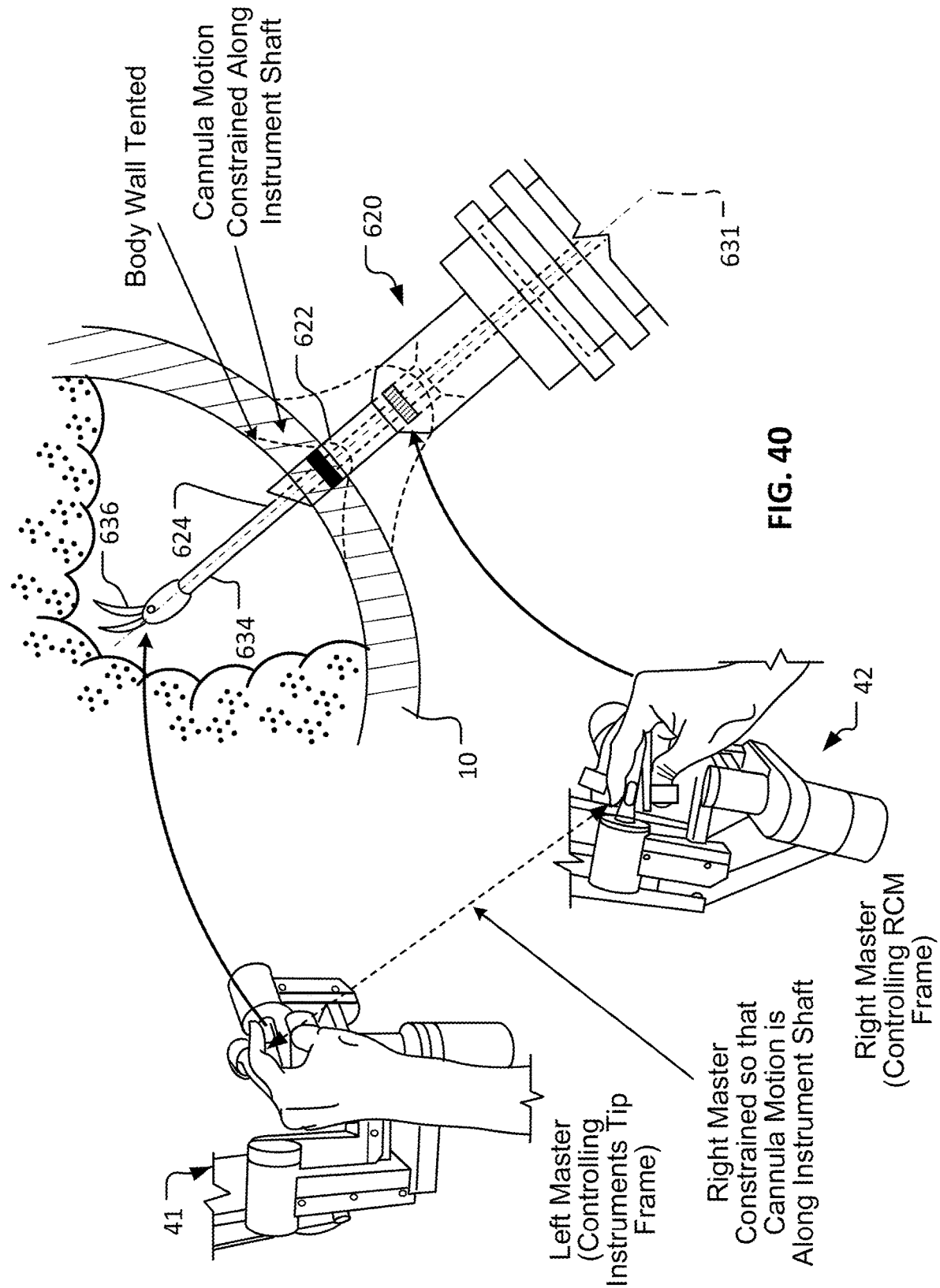
FIG. 40 illustrates an example method for implementing surgeon-controlled body wall tenting and for selectively adjusting the location of the remote center of motion.

FIG. 40 illustrates another example technique or mode that can be used to tent the body wall 10. This example allows for tele-operated body wall tenting activation, using the processor of the surgery system 600, at the surgeon console 40 (refer to FIG. 2) and, in some cases, for selectively adjusting the location of the remote center of motion using the processor of the surgery system 600. In this example, the two hands of a surgeon or other operator actuate and control the left, handheld, master input device 41 and the right, handheld, master input device 42. The left master input device 41 controls, using the processor of the surgery system 600, the movement of the end effector 636. The right master input device 42 controls, using the processor of the surgery system 600, the movement of the cannula 620 that is coupled with the body wall 10 using the tissue engagement element 624.

To activate the tenting of the body wall 10 by the processor of the surgery system 600, the surgeon simply moves the right master input device 42 away from the left master input device 41. In various embodiments, this can be achieved by moving the right master input device 42 relative to the earth while holding the left master input device 41 still relative to the earth, holding the right master input device 42 still relative to the earth while moving the left master input device 41 relative to the earth, moving, or by moving both the right and left master input devices 42, 41 relative to the earth. In result, the cannula 620 is moved away from the end effector 636. Because the cannula 620 is coupled with the body wall 10 via the tissue engagement element 624, the movement of the cannula 620 away from the patient will result in tenting of the body wall 10. In some embodiments, using the software-constrained remote center of motion concepts, the relative motion of the right master input device 42 in relation to the left master input device 41 can activate movement of the cannula 620, by the processor of the surgery system 600, along a fixed line in space that is coincident with the longitudinal axis 631 of the instrument shaft 634. Some or all of such constraint on the motion of the robotic manipulator arm assembly 610 may be imposed using, in part or in full, the robotic data processing and control techniques described herein. In some embodiments, the forces on the tissue due to tenting (determined via measurement, estimation from models, a combination of measurement and modeling, etc.) can be used by the controller of the surgery system 600 for purposes such as, to limit the movement of the remote center of motion, or to provide haptic feedback to the surgeon or other operator at the console 40. As some examples, such haptic feedback may simulate for the operator the manual manipulation of the cannula 620 to tent the body wall 10, may simulate the for the operator the reaction forces experienced by the instrument holder 614 or manipulator arm assembly 610 or other structure corresponding to the tenting of the body wall 10, or the like.

Although the left and right master devices 42, 41 are described as attached to the console 40 above, it is appreciated that, in some embodiments, other handheld input devices usable may be separate from any consoles, be ungrounded, and communicate wirelessly.

In accordance with the preceding description of FIG. 40, it can be envisioned that this disclosure describes a method to modify (change in size such as enlarge or reduce; or change in shape; or any other change to the spatial characteristics of) a surgical working space that includes receiving input from a first handheld input device away from a second handheld input device, and moving the manipulator assembly 610. In some cases, the method includes keeping the surgical instrument 630 substantially stationary while causing the manipulator assembly 610 to move such that the cannula 620 moves along the longitudinal axis of the surgical instrument 630 and modifies (such as enlarges) the surgical working space.

Figures 41, 42:
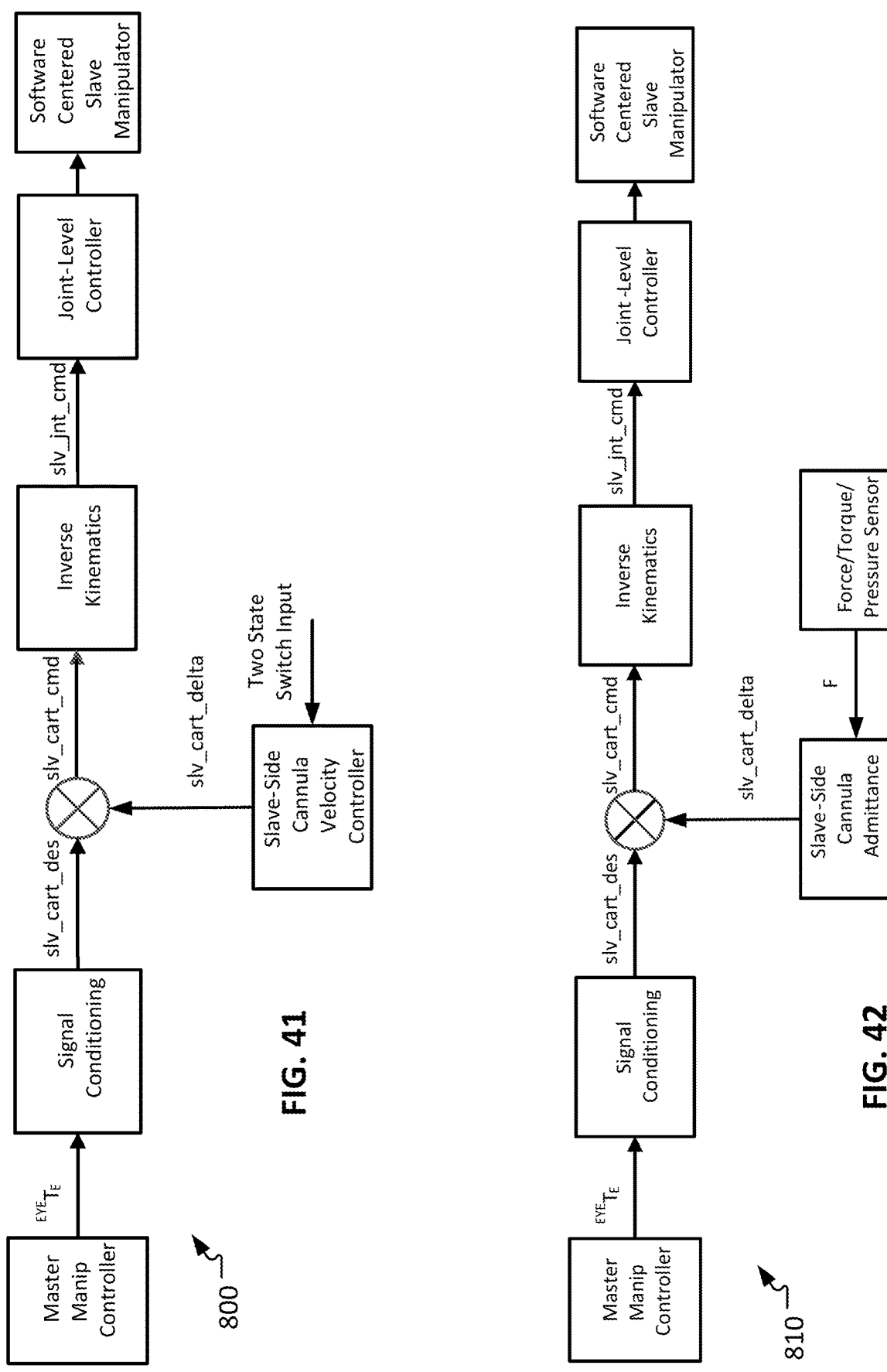
FIGS. 41 and 42 are example schematic block diagrams of two systems for controlling the relationship between the instrument end-effector frame of reference and the remote center frame of reference.

FIGS. 41 and 42, are example schematic block diagrams of two systems 800 and 810 for controlling, using the processor of a computer-assisted surgical system, the relationship between the instrument end-effector frame of reference and the remote center frame of reference. In some embodiments of these systems, the cannula and the remote center frames of reference are assumed to be coincident. Furthermore, the cannula and the remote center are physically constrained to move in relation to the instrument end-effector (only along the longitudinal axis of the cannula and the instrument). In such a case, there are two distinct strategies that may be employed to control the relationship between the frames of reference of the instrument end-effector (frame E) and the remote center (frame RC).

One strategy that can be used to actively control the relative distance (d) between the two frames of reference (regardless of whether frame E is fixed or moving) uses input from a force/torque sensor or a three-state switch. The control sub-system for this mode could be implemented using the block diagram shown in FIG. 41. This control sub-system can be described as a 'relative pose controller.' This is conceptually similar to FIG. 30 described above.

For example, FIG. 41 provides a general block diagram for relative control of cannula distance from tip using a three-state switch. In this embodiment, the incremental Cartesian command to the slave manipulator, "slv_cart_delta," may be expressed as follows: slv_cart_delta=S*slv_cart_vel*Ts (where Ts is the sampling time of the controller). S could take values [1, −1, 0], depending on whether it commands motion into the body, out of the body, or no motion. One of ordinary skill in the art will readily recognize that the incremental position control and velocity control are interchangeable and serve the same purpose.

FIG. 42 provides a general block diagram for relative control of cannula distance from the tip using a force/torque or pressure sensor. In this embodiment, the incremental Cartesian command to the slave manipulator, "slv_cart_ delta," may be expressed as follows: slv_cart_delta=f(F, p) (where "f" is a programmable function that uses as inputs the sensed force or pressure F and some user defined parameters p). This is an admittance controller. In one embodiment, this may be realized by estimating the Cartesian force along the cannula axis by means of joint torque sensors and knowledge of arm kinematics. Following such estimation, the computed estimate may be used as the input F to command the incremental motion. The signal F could be any other measured or computed force quantity based on the interaction of the user with the manipulator with the intent of moving the remote center of motion w.r.t. the end-effector.

In addition, another strategy may be used to independently control the trajectories of frames RC and E where the control inputs that govern these trajectories could both potentially come from the master manipulators. The control sub-system block diagram for this additional strategy can be known as an 'independent pose controller,' which is described in FIGS. 28-30. The trombone control mode shown in FIG. 40 is an example of this strategy.

It should be understood that insertion (I/O) motions may be generalized in some cases to allow lateral motions of the remote center or cannula with respect to the instrument tip E. In this case, in order not to affect tip pose E, the remote or cannula would need to pivot around the tip, while the instrument is driven to compensate for motion for E. This would allow for-roughly-lateral motions of the RC or cannula at the body wall and may be helpful for manipulating the surgical field in more complex ways.

Figure 43:
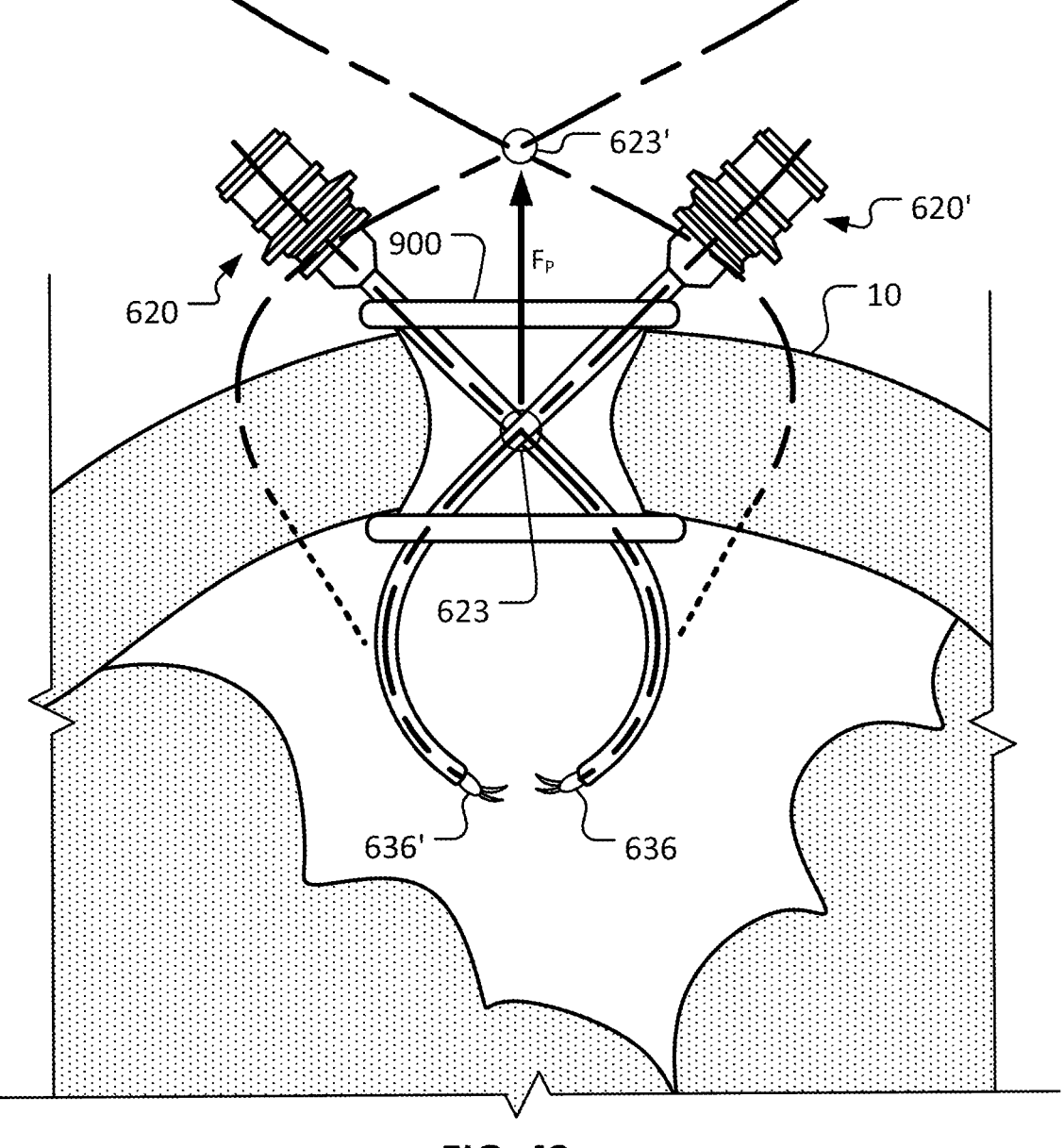
FIG. 43 illustrates a method of tenting a body wall in the context of a single site access robotic surgical technique.

Referring to FIG. 43, some minimally invasive robotic surgery methods use a single-site technique. An objective of the single-site technique is to reduce the number of incisions through the body wall 10. For example, in the depicted arrangement a first cannula 620 and a second cannula 620' each pass through separate lumens of a port device 900. The port device 900 is engaged with the body wall 10 using a single incision. Therefore, two cannulae 620 and 620' are being used via a single incision.

Using the software-constrained remote center of motion concepts described herein, movements of the two cannulae 620 and 620' can be coordinated, using the processor of the surgical system, so that the body wall 10 can be tented. It should be understood that each individual cannulae 620 and 620' are coupled to a respective robotic manipulator assembly 610 and 610' (not shown; refer to FIGS. 21 and 22).

Each of the two cannulae 620 and 620' have a shared remote center of motion. In the depicted arrangement, prior to tenting the body wall 10, the shared remote center of motion is at a first location, shown as position 623. Using the techniques described herein, the two robotic arm assemblies coupled to the two cannulae 620 and 620' can be moved in coordination so that the shared remote center of motion is moved, using the processor of the surgery system 600, to a second location 623'. In result, the port device 900 will be moved away from the patient, and the body wall 10 will become tented. During the movement of the two cannulae 620 and 620', the end effectors 636 and 636' can be maintained in generally stationary positions within the surgical working space.

In view of the above description of FIG. 43, it can be envisioned that in some embodiments the processor of the surgery system 600 is configured and/or programmed by machine-readable instructions to detect a coupling of a cannula 620 to the manipulator assembly 610 (wherein the cannula 620 is configured to couple with a tissue layer of a patient), detect a second coupling of a second cannula 620' to a second manipulator assembly 610' of the surgery system 600 (wherein the second cannula 620' is configured to couple with the tissue layer of a patient), and to move the manipulator assembly 610 and the second manipulator assembly 610' contemporaneously such that the cannula 620 and the second cannula 620' cause the tissue layer to deform and modify a surgical working space. For example, cause the tissue layer to tent and enlarge the surgical working space. In some cases, the step of moving the manipulator assembly 610 and the second manipulator assembly 610' contemporaneously includes limiting contemporaneous movement of the manipulator assembly 610 and the second manipulator assembly 610' based on a shared remote center of motion.

As additional embodiments, the robotic systems described herein (e.g. the surgery system described in conjunction with FIGS. 1-2, the surgery system 600, the various manipulator assemblies and associated processors, and the other systems) may be expanded to maintain, or to move, the pivot location in a prescribed way, while accounting for one or more other constraints on the motion of the manipulator linkage. They determine and drive motion to balance the task of maintaining or moving the pivot location with one or more tasks corresponding to motion other constraints. Examples constraints include static or dynamic limits on the position, velocity, acceleration, jerk, or any combination of the foregoing for one or more parts of the manipulator linkage. Additional example constraints include static or dynamic limits on current draw, output power, output torque, output force, sensed torque or force, etc. etc.

A number of techniques for controlling motions of robotic systems have been described in this disclosure. Many specific examples describe the techniques in the context of robotic manipulator(s), cannula(s), and surgical instrument(s) in various surgical contexts. Although most of the examples describe the techniques in conjunction with surgical operations, these techniques can also be applied to non-surgical operations including those for medical diagnosis or non-surgical treatment. Further, these techniques can also be used in non-medical robotic systems.

In some cases, it is beneficial to provide an indication of the location of the software-constrained remote center of motion. Such indications may be used singly or in combination, and with any of the embodiments described herein. Indications can be provided in various ways. For example, in some embodiments the processor of the surgery systems described herein can be configured to provide one or more visual indicators or cues of the position of the remote center of motion to the surgeon via the surgeon console, for example. In one such example, the location of the software-constrained remote center of motion can be depicted by a graphical representation in the display 45 (FIG. 2) to the surgeon or other operator or personnel. In another example, in some embodiments a light (e.g., a diffused light) can shine within the surgical working space to indicate the location of the software-constrained remote center of motion. The shining light can be viewed in the display by the surgeon (or other operator or personnel). In some embodiments, haptic feedback can be provided to indicate movements of the software-constrained remote center of motion. For example, in one such embodiment, a haptic detent can be provided for every 5 millimeter of movement of the software-constrained remote center of motion. As additional examples, sound or voice prompts with or without haptic feedback, indicate movement of the software-constrained remote center of motion.

Some examples of additional visual cues of the position of the remote center of motion that can be provided are as follows. A visual projection onto the patient's body surface or cannula that indicates the location of the remote center can be included. For example, if the projection is set to be focused to a point at the remote center, then the spot size visible at the skin surface would represent distance from the remote center. One could also use two or more rays of light that are aligned to intersect at the remote center, such that the distance between the two or more rays reflected from the skin surface indicates distance from remote center. This could be observed directly by an operator at the bedside, or via an external camera view shown in the surgical console. The projection could also be an actual number reading of the depth from the surface, where the location of the skin surface with respect to instrument manipulator may be measured using machine vision, depth camera, or some other means. The remote center location could be illuminated as a band on the cannula itself, or as a series of bands that are a known distance to either side of the remote center. This could be useful when the surgeon is at the patient side and able to observe the cannula directly.

In some embodiments, one or more safety features can be used in conjunction with the techniques for controlling motions of the robotic manipulator, cannula, and surgical instrument in the various surgical contexts that are described in this disclosure. Such indications may be used singly or in combination, and with any of the embodiments described herein. For example, in some embodiments the off-axis location of the software-constrained remote center of motion is monitored using the processor of the surgical systems described herein. The off-axis location can be constrained by the processor of the surgical system to a limit distance, and/or an alert to the surgeon can be provided when the off-axis location is beyond a threshold distance.

Another safety feature that is provided in conjunction with some embodiments is to limit, using the processor of the surgical systems described herein, the velocity of the motion of the software-constrained remote center of motion. Such a velocity limit can help to minimize the potential for tearing tissue in some circumstances. Further, another safety feature is to include force-sensing devices (e.g., a force-sensing cannula) and to use the force feedback, by the processor of the surgical systems described herein, in the control scheme for the software-constrained remote center of motion. For example, a force limit can be established such that the software-constrained remote center of motion cannot be moved farther when the force limit is reached. In some embodiments, force limits can be used in combination with distance limits. To provide feedback to the clinicians, in some embodiments the system can sound an alert when the limit is reached, or neared (e.g., haptics, auditory, visual, tactile, etc.).

Additional safety features that can be used in conjunction with some embodiments include constraining, by the processor of the surgical systems described herein, the movement of the software-constrained remote center of motion to be only along the cannula, or only along the shaft of the surgical instrument.

In some embodiments, a camera can be used on the outside of the patient so that the surgeon can see the extent of the tissue tenting. For example, in some embodiments, a picture-in-picture can be used with the display at the surgeon console. That is, a video picture of the tenting taken by the camera on the outside of the patient can be fed to the display of the surgeon console while still allowing the surgeon to see the images from the endoscope being used for the surgery. Such a display may be used with any of the embodiments described herein.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A computer-assisted system comprising:
a manipulator assembly configured to couple to a cannula at a distal portion of the manipulator assembly, the cannula having a lumen configured to receive a shaft of an instrument, wherein a cannula axis is aligned with the cannula when the cannula is coupled to the manipulator assembly, and wherein an instrument axis is aligned with the instrument when the instrument is coupled to the manipulator assembly; and
a controller coupled to the manipulator assembly;
wherein the controller is configured to:
receive a first indication to reposition a remote center of motion for the manipulator assembly while the remote center of motion is positioned at a first location relative to the distal portion along a first axis, wherein the first axis is aligned with the cannula axis or the instrument axis, and
in response to receiving the first indication, cause the remote center of motion to be positioned at a second location relative to the distal portion along the first axis, wherein the second location relative to the distal portion is different from the first location relative to the distal portion.

2. The computer-assisted system of claim 1, wherein the cannula axis is coincident with a longitudinal axis of the cannula or a longitudinal axis of the lumen, or wherein the instrument axis is coincident with a longitudinal axis of the shaft of the instrument.

3. The computer-assisted system of claim 1, wherein the controller is further configured to:

in response to receiving a second indication to reposition the remote center of motion while the remote center of motion is positioned at the first location relative to the distal portion along the first axis, cause the remote center of motion to be positioned at a third location relative to the distal portion, wherein the third location is not along the first axis.

4. The computer-assisted system of claim 1, wherein the controller is further configured to:

receive, after the remote center of motion has been positioned at the second location, a command to move the instrument according to a commanded motion; and command the instrument to move with a modified motion, the modified motion being based on the commanded motion and the second location.

5. The computer-assisted system of claim 1, wherein the controller is further configured to constrain the second location to be along the cannula.

6. The computer-assisted system of claim 1, wherein the controller is further configured to:

command the manipulator assembly to cause relative motion of the cannula and the instrument such that the first location and the second location are at a same location relative to the instrument.

7. The computer-assisted system of claim 1, wherein to cause the remote center of motion to be positioned at the second location, the controller is further configured to:

reposition the remote center of motion to the second location while limiting a speed of motion of the remote center of motion.

8. The computer-assisted system of claim 1, wherein the controller is further configured to:

prevent repositioning of the remote center of motion in response to a force associated with the cannula exceeding a force limit.

9. The computer-assisted system of claim 1, wherein the controller is further configured to:

move the cannula relative to a patient to modify a medical working space accessed by the lumen of the cannula.

10. A method for positioning a remote center of motion for a manipulator assembly of a computer-assisted system, wherein the manipulator assembly is configured to couple to a cannula at a distal portion, wherein the cannula has a lumen configured to receive a shaft of an instrument, wherein a cannula axis is aligned with the cannula when the cannula is coupled to the manipulator assembly, and wherein an instrument axis is aligned with the instrument when the instrument is coupled to the manipulator assembly, the method comprising:

receiving, by a controller of the computer-assisted system and while the remote center of motion is positioned at a first location relative to the distal portion along a first axis, a first indication to reposition the remote center of motion, wherein the first axis is aligned with the cannula axis or the instrument axis; and causing, in response to receiving the first indication and by the controller, the remote center of motion to be positioned at a second location relative to the distal portion along the first axis, wherein the second location is different from the first location relative to the distal portion.

11. The method of claim 10, wherein the cannula axis is coincident with a longitudinal axis of the cannula or a longitudinal axis of the lumen, or wherein the instrument axis is coincident with a longitudinal axis of the instrument.

12. The method of claim 10, further comprising:

causing, in response to receiving a second indication to reposition the remote center of motion while the remote center of motion is positioned at the first location relative to the distal portion along the first axis and by the controller, the remote center of motion to be positioned at a third location relative to the distal portion, wherein the third location is not along the first axis.

13. The method of claim 10, further comprising:

constraining, by the controller, the second location to be along the cannula.

14. The method of claim 10, further comprising:

commanding, by the controller, the manipulator assembly to cause relative motion of the cannula and the instrument relative to each other such that the first location and the second location are at a same location relative to the instrument.

15. The method of claim 10, wherein causing the remote center of motion to be positioned at the second location comprises:

repositioning the remote center of motion to the second location while limiting a speed of motion of the remote center of motion.

16. The method of claim 10, further comprising:

preventing, by the controller, repositioning of the remote center of motion in response to a force associated with the cannula exceeding a force limit.

17. A non-transitory machine-readable medium comprising a plurality of machine-readable instructions which, when executed by one or more processors associated with a computer-assisted system comprising a manipulator assembly, are adapted to cause the one or more processors to perform a method comprising:

receiving, while a remote center of motion for the manipulator assembly of the computer-assisted system is positioned at a first location relative to a distal portion of the manipulator assembly along a first axis, an indication to reposition the remote center of motion, wherein the manipulator assembly is configured to couple to a cannula at the distal portion, wherein the cannula has a lumen configured to receive a shaft of an instrument, wherein a cannula axis is aligned with the cannula when the cannula is coupled to the manipulator assembly, wherein an instrument axis is aligned with the instrument when the instrument is coupled to the manipulator assembly, and wherein the first axis is aligned with the cannula axis or the instrument axis; and in response to receiving the indication, causing the remote center of motion to be positioned at a second location relative to the distal portion along the first axis, wherein the second location is different from the first location relative to the distal portion.

18. The non-transitory machine-readable medium of claim 17, wherein the cannula axis is coincident with a longitudinal axis of the cannula or a longitudinal axis of the lumen, or wherein the instrument axis is coincident with a longitudinal axis of the instrument.

19. The non-transitory machine-readable medium of claim 17, wherein causing the remote center of motion to be positioned at the second location comprises:

repositioning the remote center of motion to the second location while limiting a speed of motion of the remote center of motion.

20. The non-transitory machine-readable medium of claim 17, wherein the method further comprises:

preventing repositioning of the remote center of motion in response to a force associated with the cannula exceeding a force limit.

* * * * *